(12) United States Patent
Handa et al.

(10) Patent No.: US 11,993,629 B2
(45) Date of Patent: May 28, 2024

(54) METHOD FOR PRODUCING PEPTIDE COMPOUND

(71) Applicants: NISSAN CHEMICAL CORPORATION, Tokyo (JP); PeptiDream Inc., Kawasaki (JP)

(72) Inventors: Michiharu Handa, Funabashi (JP); Naohiko Yasuda, Funabashi (JP); Akihiro Nagaya, Funabashi (JP); Hiroyuki Kousaka, Funabashi (JP)

(73) Assignees: Nissan Chemical Corporation, Tokyo (JP); PeptiDream Inc., Kawasaki (JP)

( * ) Notice: Subject to any disclaimer, the term of this patent is extended or adjusted under 35 U.S.C. 154(b) by 0 days.

(21) Appl. No.: 17/427,910

(22) PCT Filed: Feb. 3, 2020

(86) PCT No.: PCT/JP2020/003927
§ 371 (c)(1),
(2) Date: Aug. 2, 2021

(87) PCT Pub. No.: WO2020/162393
PCT Pub. Date: Aug. 13, 2020

(65) Prior Publication Data
US 2022/0106355 A1 Apr. 7, 2022

(30) Foreign Application Priority Data

Feb. 4, 2019 (JP) .................................. 2019-017919
Nov. 19, 2019 (JP) .................................. 2019-209066

(51) Int. Cl.
*C07K 1/06* (2006.01)
(52) U.S. Cl.
CPC .................................. *C07K 1/063* (2013.01)
(58) Field of Classification Search
CPC .......... C07K 1/063; C07K 1/088; Y02P 20/55
See application file for complete search history.

(56) References Cited

U.S. PATENT DOCUMENTS 5,714,484 A 2/1998 Zimmerman et al.

FOREIGN PATENT DOCUMENTS

| JP | H04-502908 A | 5/1992 |
|---|---|---|
| JP | 2004-067555 A | 3/2004 |
| JP | 2004067555 A * | 3/2004 |
| JP | 5535928 B2 | 7/2014 |
| WO | WO 1990/005738 A1 | 5/1990 |
| WO | WO 2009/065836 A1 | 5/2009 |

OTHER PUBLICATIONS

Isidro-Llobet et al (Chem.Rev., 2009, 109, 2455-2504) (Year: 2009).*
Liang et al., "Di-tert-butylisobutylsilyl, Another Useful Protecting Group," *Org. Lett.*, 13(15): 4120-4123 (2011).
Lipshutz et al., "Triisopropylsilyloxycarbonyl ('Tsoc'): A New Protecting Group for 1° and 2° Amines," *J. Org. Chem.*, 64(11): 3792-3793 (1999).
Lipshutz et al., "A new silyl linker for reverse-direction solid-phase peptide synthesis," *Tetrahedron Lett.*, 42(33): 5629-5633 (2001).
Sakamoto et al., "Combination of silyl carbamate and amino acid fluoride for solid-phase peptide synthesis," *Tetrahedron Lett.*, 43(8): 1515-1518 (2002).
Tanaka et al., "Catalytic dehydrogenative N-((triisopropylsilyl)oxy)-carbonyl (Tsoc) protection of amines using iPr₃SiH and CO₂," *Chem. Comm.*, 51(66): 13110-13112 (2015).
Japanese Patent Office, International Search Report in International Patent Application No. PCT/JP2020/003927 (dated Mar. 31, 2020).
Katayama et al., "Direct Evidence for the Function of Crustacean Insulin-like Androgenic Gland Factor (IAG): Total Chemical Synthesis of IAG," *Bioorg. Med. Chem.*, 22(21): 5783-5789 (2014).
European Patent Office, Extended European Search Report in European Patent Application No. 20752714.4 (dated Oct. 31, 2022).
Japan Patent Office, Office Action in Japanese Patent Application No. 2020-571181 (dated Nov. 21, 2023).

* cited by examiner

*Primary Examiner* — Sudhakar Katakam
(74) *Attorney, Agent, or Firm* — Leydig, Voit & Mayer, Ltd.

(57) ABSTRACT

The invention provides a method for producing a peptide which comprises the following steps (1) and (2): (1) a step of condensing a C-protected amino acid or a C-protected peptide to a C-terminal of an N-protected amino acid or an N-protected peptide represented by the formula (I):

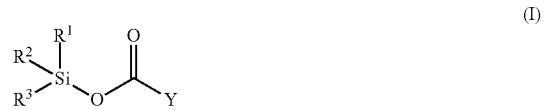

(I)

wherein Y represents an amino acid in which a C-terminal is unprotected or a peptide in which a C-terminal is unprotected, $R^1$, $R^2$ and $R^3$ each independently represent an aliphatic hydrocarbon group which may have a substituent(s), a total number of the carbon atoms in the $R^1R^2R^3$Si group is 10 or more, and the $R^1R^2R^3$SiOC(O) group is bonded to the N-terminal in Y, and (2) a step of removing the protective group at the C-terminal of the peptide obtained in step (1).

39 Claims, No Drawings

METHOD FOR PRODUCING PEPTIDE COMPOUND

CROSS-REFERENCE TO RELATED APPLICATIONS

This patent application is the U.S. national phase of International Patent Application No. PCT/JP2020/003927, filed on Feb. 3, 2020, which claims the benefit of Japanese Patent Application No. 2019-017919, filed on Feb. 4, 2019, and Japanese Patent Application No. 2019-209066, filed on Nov. 19, 2019, which are incorporated by reference in their entireties herein.

TECHNICAL FIELD

The present invention relates to a novel method for producing a peptide using a silylcarbamate-based protective group.

BACKGROUND ART

A silylcarbamate-based protective group can be deprotected by a fluorine ion, etc., mild and selectively to the other protective groups, so that it has been used for peptide synthesis as an N-terminal protective group of amino acids and peptides (for example, Non-Patent Documents 1 to 3).

As a representative example of use in peptide synthesis, it has been known a method in which an amino acid the N-terminal side of which is protected with a triisopropylsilylcarbonyl (Tsoc) group and an amino acid the C-terminal of which is protected are condensed to obtain a dipeptide the N-terminal and the C-terminal of which are protected (for example, Non-Patent Documents 1 and 2).

As another example of use in peptide synthesis, it has been known a solid phase synthesis method in which the N-terminal side is bound to a silyl carbamate-based solid phase support, and then, a peptide chain is elongated to the C-terminal side (for example, Non-Patent Document 3).

Also, as a method for elongating peptide chain to the C-terminal side, it has been known a method in which the C-terminal carboxy group is activated by an alkyl chloroformate, and reacting it with a silylated amino acid or peptide to obtain a peptide having a liberated C-terminal (for example, Patent Documents 1 and 2).

PRIOR ART DOCUMENTS

Patent Documents

Patent Document 1: JP Patent No. 5,535,928
Patent Document 2: U.S. Pat. No. 5,714,484

Non-Patent Documents

Non-Patent Document 1: Tetrahedron Letters, 2002, vol. 43, pp. 1515-1518
Non-Patent Document 2: Journal of Organic Chemistry, 1999, vol. 64, pp. 3792-3793
Non-Patent Document 3: Tetrahedron Letters, 2001, vol. 42, pp. 5629-5633

SUMMARY OF THE INVENTION

Problems to be Solved by the Invention

In the peptide synthesis of the above-mentioned Non-Patent Document 1, a peptide in which the C-terminal is liberated has not been obtained, and further, it was not investigated with regard to the method of elongating a peptide chain to the C-terminal side while maintaining the bond between the N-terminal and the silylcarbamate-based protective group.

Also, according to the method of the above-mentioned Non-Patent Document 2, a peptide in which the C-terminal is liberated has not been obtained, and further, it has found that a Tsoc group of the N-terminal protective group can be easily eliminated by removal of the C-terminal protective group or a liquid separating operation under acidic and basic conditions.

The present invention is to provide a novel method for producing a peptide in a liquid phase by elongating a peptide chain to a C-terminal side using a silylcarbamate-based protective group having a specific structure at an N-terminal side to obtain a peptide in which the C-terminal is liberated.

Means to Solve the Problems

The present inventors have intensively studied, and as a result, they have found that the above-mentioned problems can be solved by using a silylcarbamate-based protective group having a specific structure, whereby the present invention has accomplished. That is, the present invention has the following characteristics.

[1]
A method for producing a peptide which comprises the following Steps (1) and (2).
(1)
A step of condensing a C-protected amino acid or a C-protected peptide to a C-terminal of an N-protected amino acid or an N-protected peptide represented by the formula (I):

[wherein,
Y represents an amino acid in which a C-terminal is unprotected or a peptide in which a C-terminal is unprotected,
$R^1$, $R^2$ and $R^3$ each independently represent an aliphatic hydrocarbon group which may have a substituent(s), a total number of the carbon atoms in the $R^1R^2R^3Si$ group is 10 or more, and the $R^1R^2R^3SiOC(O)$ group is bonded to an N-terminal in Y.].
(2)
A step of removing the protective group at the C-terminal of the peptide obtained in Step (1).
[2]
The producing method described in [1], which further comprises one or more repeating the following Steps (3) and (4).
(3)
A step of condensing the C-protected amino acid or the C-protected peptide to the C-terminal of the peptide obtained in Step (2) or (4).
(4)
A step of removing the protective group at the C-terminal of the peptide obtained in Step (3).

[3]

The producing method described in [1] or [2], which comprises a step of purifying the obtained peptide by liquid separating.

[4]

The producing method described in [1] or [2], which comprises a step of purifying the obtained peptide by liquid separating with an acidic aqueous solution or a basic aqueous solution.

[5]

The producing method described in any one of [1] to [4], wherein the protective group at the C-terminal of the C-protected amino acid or the C-protected peptide is a $C_{1-6}$ alkyl group, a $C_{7-10}$ aralkyl group or a tri-$C_{1-6}$ alkylsilyl group.

[6]

The producing method described in any one of [1] to [4], wherein the protective group at the C-terminal of the C-protected amino acid or the C-protected peptide is a $C_{1-6}$ alkyl group or a tri-$C_{1-6}$ alkylsilyl group.

[7]

The producing method described in any one of [1] to [4], wherein the protective group at the C-terminal of the C-protected amino acid or the C-protected peptide is a tri-$C_{1-6}$, alkylsilyl group.

[8]

The producing method described in any one of [1] to [4], wherein the protective group at the C-terminal of the C-protected amino acid or the C-protected peptide is a tri-methylsilyl group.

[9]

The producing method described in any one of [1] to [8], wherein the condensation in Step (1) is carried out using a condensation agent selected from the group consisting of a carbodiimide-based condensation agent, a chloroformate-based condensation agent, an acid halide-based condensation agent, a phosphonium-based condensation agent and an uronium-based condensation agent.

[10]

The producing method described in any one of [1] to [8], wherein the condensation in Step (1) is carried out using a condensation agent selected from the group consisting of isobutyl chloroformate, pivaloyl chloride and (1-cyano-2-ethoxy-2-oxoethylideneaminooxy)dimethylamino-morpholino-carbenium hexafluorophosphate.

[11]

The producing method described in any one of [1] to [10], wherein a base is further used in Step (1).

[12]

The producing method described in [11], wherein the base is an aliphatic amine or an aromatic amine.

[13]

The producing method described in [11], wherein the base is N,N-diisopropyl-ethylamine or N-methylmorpholine.

[14]

The producing method described in any one of [1] to [13], wherein the deprotection conditions in Step (2) are conditions using a deprotecting agent other than the fluorine compound.

[15]

The producing method described in any one of [1] to [13], wherein the deprotection conditions in Step (2) are conditions using water, a base or an acid, or using hydrogen and a metal catalyst.

[16]

The producing method described in any one of [1] to [13], wherein the deprotection conditions in Step (2) are conditions using water, trifluoroacetic acid or lithium hydroxide, or using hydrogen and palladium carbon powder.

[17]

The producing method described in any one of [7] to [13], wherein the deprotection conditions in Step (2) are conditions using water.

[18]

The producing method described in any one of [1] to [17], which further comprises the following Step (5).

(5) a step of removing the protective group at the N-terminal of the peptide obtained in Step (2) or (4) with a deprotecting agent.

[19]

The producing method described in [18], wherein the deprotecting agent using in Step (5) is a fluorine compound.

[20]

The producing method described in [19], wherein the fluorine compound is potassium fluoride or ammonium fluoride.

[21]

The producing method described in any one of [1] to [17], which further comprises the following Steps (6) and (7).

(6)

A step of condensing a C-protected amino acid or C-protected peptide to the C-terminal of the peptide obtained in Step (2) or (4).

(7)

A step of removing the protective group at the N-terminal of the peptide obtained in Step (6) with a deprotecting agent.

[22]

The producing method described in [21], wherein the deprotecting agent using in Step (7) is a fluorine compound.

[23]

The producing method described in [22], wherein the fluorine compound is potassium fluoride or ammonium fluoride.

[24]

The producing method described in any one of [21] to [23], wherein the protective group at the C-terminal of the C-protected amino acid or the C-protected peptide is a $C_{1-6}$ alkyl group or a benzyl group.

[25]

The producing method described in any one of [1] to [24], wherein a total number of the carbon atoms in the $R^1R^2R^3Si$ group is 10 to 100.

[26]

The producing method described in any one of [1] to [24], wherein a total number of the carbon atoms in the $R^1R^2R^3Si$ group is 10 to 40.

[27]

The producing method described in any one of [1] to [24], wherein a total number of the carbon atoms in the $R^1R^2R^3Si$ group is 12 to 26.

[28]

The producing method described in any one of [1] to [27], wherein two or three of $R^1$, $R^2$ and $R^3$ are each independently a secondary or tertiary aliphatic hydrocarbon group.

[29]

The producing method described in [28], wherein two of $R^1$, $R^2$ and $R^3$ are each independently a secondary aliphatic hydrocarbon group, and the remaining one is a tertiary aliphatic hydrocarbon group.

[30]

The producing method described in [29], wherein two of $R^1$, $R^2$ and $R^3$ are each independently a secondary $C_{3-6}$ alkyl group, and the remaining one is a tertiary $C_{4-6}$ alkyl group.

[31]

The producing method described in any one of [1] to [26], wherein the $R^1R^2R^3Si$ group is a di-i-propyl-t-butylsilyl group.

[32]

The producing method described in [28], wherein two of $R^1$, $R^2$ and $R^3$ are each independently secondary aliphatic hydrocarbon groups, and the remaining one is a secondary aliphatic hydrocarbon group having a substituent(s) (wherein the substituent(s) of the secondary aliphatic hydrocarbon group exists on the carbon atom bonded to the silyl atom.).

[33]

The producing method described in [32], wherein two of $R^1$, $R^2$ and $R^3$ are each independently secondary $C_{3-6}$ alkyl groups, and the remaining one is a secondary $C_{3-6}$ alkyl group substituted by a phenyl group(s) (wherein the phenyl group which is the substituent(s) of the secondary $C_{3-6}$ alkyl group exists on the carbon atom bonded to the silyl atom.).

[34]

The producing method described in [33], wherein the $R^3R^2R^3Si$ group is a di-i-propylcumylsilyl group.

[35]

The producing method described in [28], wherein two of $R^1$, $R^2$ and $R^3$ are each independently a tertiary aliphatic hydrocarbon group.

[36]

The producing method described in [35], wherein two of $R^1$, $R^2$ and $R^3$ are each independently a tertiary $C_{4-6}$ alkyl group.

[37]

The producing method described in [36], wherein the $R^3R^2R^3Si$ group is a di-t-butylisobutylsilyl group.

[38]

The producing method described in [36], wherein the $R^3R^2R^3Si$ group is a benzyl-di-t-butylsilyl group, a di-t-butyloctadecylsilyl group or a di-t-butylcyclo-hexylsilyl group.

[39]

The producing method described in any one of [1] to [38], wherein the amino acid or the peptide consists of an α-amino acid(s).

Effects of the Invention

According to the present invention, it could be provided a novel method for producing a peptide using a silylcarbamate-based protective group in a liquid phase.

EMBODIMENTS TO CARRY OUT THE INVENTION

Hereinafter, the present invention will be explained in detail.

In the present specification, "n-" means normal, "i-" means iso, "s-" means secondary, "t-" means tertiary, "Me" means methyl, "Bu" means butyl, "Bn" means benzyl, "Ph" means phenyl, "Tf" means trifluoromethanesulfonyl, "TMS" means trimethylsilyl, "IPBS" means di-i-propyl-t-butylsilyl, "IPCS" means di-i-propyl-cumylsilyl, "PhBS" means di-t-butylphenylsilyl, "CHBS" means di-t-butylcyclohexylsilyl, "Tsoc" means triisopropylsilyloxycarbonyl, "BIBSoc" means di-t-butylisobutylsilyloxycarbonyl, "IPBSoc" means di-i-propyl-t-butylsilyloxycarbonyl, "IPCSoc" means di-i-propylcumylsilyloxycarbonyl, "BBSoc" means benzyl-di-t-butylsilyloxycarbonyl, "CHBSoc" means di-t-butylcyclohexylsilyloxycarbonyl, "ODBSoc" means di-t-butyloctadecylsilyloxycarbonyl, and "Boc" means t-butyloxycarbonyl.

The terms "halogen atom" mean a fluorine atom, a chlorine atom, a bromine atom or an iodine atom.

The terms "$C_{1-6}$ alkyl group" mean a linear or branched alkyl group having 1 to 6 carbon atoms, and specific examples thereof may be mentioned a methyl group, an ethyl group, an n-propyl group, an isopropyl group, an n-butyl group, an isobutyl group, an s-butyl group, a t-butyl group, an n-pentyl group, an n-hexyl group, etc. Also, the terms "$C_{3-6}$ alkyl group" mean a linear or branched alkyl group having 3 to 6 carbon atoms, and "$C_{4-6}$ alkyl group" mean those having 4 to 6 carbon atoms.

The terms "$C_{1-40}$ alkyl group" mean a linear or branched alkyl group having 1 to 40 carbon atoms, and specific examples thereof may be mentioned a methyl group, an ethyl group, an n-propyl group, an isopropyl group, an n-butyl group, an isobutyl group, an s-butyl group, a t-butyl group, an n-pentyl group, an n-hexyl group, an octyl group, a decyl group, a dodecyl group, a hexadecyl group, an octadecyl group, a docosyl group, a triacontyl group, a tetracontyl group, a 3,7,11,15-tetramethylhexadecyl group (hereinafter it may sometimes refer to a 2,3-dihydrophytyl group.), etc.

The terms "$C_{1-6}$ alkoxy group" mean a linear or branched alkoxy group having 1 to 6 carbon atoms, and specific examples thereof may be mentioned a methoxy group, an ethoxy group, an n-propoxy group, an isopropoxy group, an n-butoxy group, an isobutoxy group, a t-butoxy group, an n-pentyloxy group, an n-hexyloxy group, etc.

The terms "$C_{1-40}$ alkoxy group" mean a linear or branched alkoxy group having 1 to 40 carbon atoms, and specific examples thereof may be mentioned a methoxy group, an ethoxy group, an n-propoxy group, an isopropoxy group, an n-butoxy group, an isobutoxy group, a t-butoxy group, an n-pentyloxy group, an n-hexyloxy group, an octyloxy group, a decyloxy group, a dodecyloxy group, a hexadecyloxy group, an octadecyloxy group, a docosyloxy group, a triacontyloxy group, a tetracontyloxy group, a 3,7,11,15-tetramethylhexadecyloxy group (hereinafter it may sometimes refer to a 2,3-dihydrophytyloxy group.), etc.

The terms "$C_{1-6}$ alkoxy carbonyl group" mean a group in which a "$C_{1-6}$ alkoxy group" is bonded to a carbonyl group, and specific examples thereof may be mentioned a methoxycarbonyl group, an ethoxycarbonyl group, an n-propoxycarbonyl group, an isopropoxycarbonyl group, an n-butoxycarbonyl group, an isobutoxycarbonyl group, a t-butoxycarbonyl group, an n-pentyloxycarbonyl group, an n-hexyloxycarbonyl group, etc.

The terms "$C_{2-6}$ alkenyl group" mean a linear or branched alkenyl group having 2 to 6 carbon atoms, and specific examples thereof may be mentioned a vinyl group, a 1-propenyl group, an allyl group, an isopropenyl group, a butenyl group, an isobutenyl group, etc.

The terms "$C_{2-6}$ alkynyl group" mean a linear or branched alkynyl group having 2 to 6 carbon atoms, and specific examples thereof may be mentioned an ethynyl group, a 1-propynyl group, etc.

The terms "$C_{3-6}$ cycloalkyl group" mean a cycloalkyl group having 3 to 6 carbon atoms, and specific examples thereof may be mentioned a cyclopropyl group, a cyclobutyl group, a cyclopentyl group, a cyclohexyl group, etc.

The terms "$C_{3-6}$ cycloalkoxy group" mean a cycloalkoxy group having 3 to 6 carbon atoms, and specific examples thereof may be mentioned a cyclopropoxy group, a cyclobutoxy group, a cyclopentyloxy group, a cyclohexyloxy group, etc.

The terms "$C_{6-14}$ aryl group" mean an aromatic hydrocarbon group having 6 to 14 carbon atoms, and specific examples thereof may be mentioned a phenyl group, a 1-naphthyl group, a 2-naphthyl group, a 1-anthracenyl group, a 2-anthracenyl group, a 9-anthracenyl group, a biphenyl group, etc.

The terms "$C_{6-14}$ aryloxy group" mean an aryloxy group having 6 to 14 carbon atoms, and specific examples thereof may be mentioned a phenoxy group, a 1-naphthyloxy group, a 2-naphthyloxy group, a 1-anthracenyloxy group, a 2-anthracenyloxy group, a 9-anthracenyloxy group, a biphenyloxy group, etc.

The terms "$C_{7-10}$ aralkyl group" mean an aralkyl group having 7 to 10 carbon atoms, and specific examples thereof may be mentioned a benzyl group, a 1-phenylethyl group, a 2-phenylethyl group, a 1-phenylpropyl group, etc.

The terms "tri-$C_{1-6}$ alkylsilyl group" mean a group in which the same or different above-mentioned three "$C_{1-6}$ alkyl group"s are bonded to the silyl group, and specific examples thereof may be mentioned a trimethyl silyl group, a triethylsilyl group, a triisopropyl silyl group, a t-butyldimethylsilyl group, a di-t-butylisobutylsilyl group, etc.

The terms "tri-$C_{1-6}$ alkylsilyloxy group" mean a group in which the same or different above-mentioned three "$C_{1-6}$ alkyl group"s are bonded to the silyloxy group, and specific examples thereof may be mentioned a trimethylsilyloxy group, a triethylsilyloxy group, a triisopropylsilyloxy group, a t-butyldimethylsilyloxy group, a di-t-butylisobutylsilyloxy group, etc.

The terms "mono-$C_{1-6}$ alkylamino group" mean a group in which the above-mentioned one "$C_{1-6}$ alkyl group" is bonded to the amino group, and specific examples thereof may be mentioned monomethylamino group, a monoethylamino group, a mono-n-propylamino group, a monoisopropylamino group, a mono-n-butylamino group, a monoisobutylamino group, a mono-t-butylamino group, a mono-n-pentylamino group, a mono-n-hexylamino group, etc.

The terms "di-$C_{1-6}$ alkylamino group" mean a group in which the same or different above-mentioned two "$C_{1-6}$ alkyl group"s are bonded to the amino group, and specific examples thereof may be mentioned a dimethylamino group, a diethylamino group, a di-n-propylamino group, a diisopropylamino group, a di-n-butylamino group, a diisobutylamino group, a di-t-butylamino group, a di-n-pentylamino group, a di-n-hexylamino group, an N-ethyl-N-methylamino group, an N-methyl-N-n-propylamino group, an N-isopropyl-N-methylamino group, an N-n-butyl-N-methylamino group, an N-isobutyl-N-methylamino group, an N-t-butyl-N-methylamino group, an N-methyl-N-n-pentylamino group, an N-n-hexyl-N-methylamino group, an N-ethyl-N-n-propyl-amino group, an N-ethyl-N-isopropylamino group, an N-n-butyl-N-ethylamino group, an N-ethyl-N-isobutylamino group, an N-t-butyl-N-ethylamino group, an N-ethyl-N-n-pentylamino group, an N-ethyl-N-n-hexylamino group, etc.

The terms "5-10-membered heterocyclic group" mean a monocyclic-based or a fused ring-based heterocyclic group having a number of the atoms constituting the ring of 5 to 10, and containing 1 to 4 hetero atoms independently selected from the group consisting of a nitrogen atom, an oxygen atom and a sulfur atom in the atoms constituting the ring. The heterocyclic group may be either of saturated, partially unsaturated or unsaturated, and specific examples thereof may be mentioned a pyrrolidinyl group, a tetrahydrofuryl group, a tetrahydrothienyl group, a piperidyl group, a tetrahydropyranyl group, a tetrahydrothiopyranyl group, a pyrrole group, a furyl group, a thienyl group, a pyridyl group, a pyrimidinyl group, a pyridazinyl group, an azepanyl group, an oxepanyl group, a thiepanyl group, an azepinyl group, an oxepinyl group, a thiepinyl group, an imidazolyl group, a pyrazolyl group, an oxazolyl group, a thiazolyl group, an imidazolinyl group, a pyrazinyl group, a morpholinyl group, a thiazinyl group, an indolyl group, an isoindolyl group, a benzimidazolyl group, a purinyl group, a quinolyl group, an isoquinolyl group, a quinoxalinyl group, a cinnolinyl group, a pteridinyl group, a chromenyl group, an isochromenyl group, etc.

The terms "aliphatic hydrocarbon group" mean a linear, branched or cyclic, saturated or unsaturated aliphatic hydrocarbon group, and there may be mentioned an alkyl group, a cycloalkyl group, alkenyl group, an alkynyl group, an aralkyl group, etc., and specific examples thereof may be mentioned a $C_{1-40}$ alkyl group, a $C_{3-6}$ cycloalkyl group, a $C_{2-6}$ alkenyl group, a $C_{2-6}$ alkynyl group, a $C_{7-10}$ aralkyl group, etc.

The terms "aromatic hydrocarbon group" are a mono- or polycyclic hydrocarbon group, and mean a group at least one ring of which shows aromaticity, and specific examples thereof may be mentioned a phenyl group, a naphthyl group, an anthracenyl group, an indenyl group, a phenacenyl group, an indanyl group, etc.

The terms "which may have a substituent(s)" mean that it is unsubstituted, or substituted by an optional number of an optional substituent(s).

The kind of the above-mentioned "optional substituent(s)" is/are not specifically limited as long as it does not exert any bad effect to the reaction targeted by the present invention.

As the "substituent" in the "aliphatic hydrocarbon group which may have a substituent(s)", there may be mentioned, for example, a $C_{6-14}$ aryl group, a $C_{6-14}$ aryloxy group, a 5 to 10-membered heterocyclic group, a hydroxy group, a $C_{1-40}$ alkoxy group, a $C_{3-6}$ cycloalkoxy group, an acetoxy group, a benzoyloxy group, an amino group, a mono-$C_{1-6}$ alkylamino group, an N-acetylamino group, a di-$C_{1-6}$ alkylamino group, a halogen atom, a $C_{1-6}$ alkoxycarbonyl group, a phenoxycarbonyl group, an N-methyl-carbamoyl group, an N-phenylcarbamoyl group, a tri-$C_{1-6}$ alkylsilyl group, a tri-$C_{1-6}$ alkylsilyloxy group, a cyano group, a nitro group, a carboxy group, etc., preferably a $C_{6-14}$ aryl group, a $C_{1-40}$ alkoxy group, a di-$C_{1-6}$ alkylamino group, a tri-$C_{1-6}$ alkylsilyl group, a tri-$C_{1-6}$ alkylsilyloxy group, and more preferably a $C_{6-14}$ aryl group, a $C_{1-40}$ alkoxy group or a tri-$C_{1-6}$ alkylsilyl group.

The terms "which has a substituent(s)" mean that it is substituted by an optional number of an optional substituent(s).

The kind of the above-mentioned "optional substituent(s)" is/are not specifically limited as long as it does not exert any bad effect to the reaction targeted by the present invention.

As the "substituent" in the "secondary aliphatic hydrocarbon group having a substituent", there may be mentioned, for example, a $C_{6-14}$ aryl group, a $C_{6-14}$ aryloxy group, a 5 to 10-membered heterocyclic group, a $C_{1-40}$ alkoxy group, a $C_{3-6}$ cycloalkoxy group, etc., preferably a $C_{6-14}$ aryl group, and more preferably a phenyl group.

In the present specification, the terms "silylcarbamate-based protective group having a specific structure" mean a protective group which binds to the N-terminal of the amino acid or peptide, represented by the following formula (II):

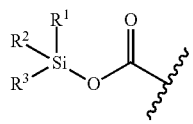

(II)

[wherein,

R¹, R² and R³ each independently represent an aliphatic hydrocarbon group which may have a substituent(s), and a total number of the carbon atoms in the R¹R²R³Si group is 10 or more.].

The terms "total number of the carbon atoms in the R¹R²R³Si group" mean a sum of the number of the carbon atoms possessed by the respective R¹, R² and R³, and when at least one of R¹, R² and R³ has a substituent(s), the number of the carbon atoms of the substituent(s) is also included.

In the formula (II), R¹, R² and R³ are each independently an aliphatic hydrocarbon group which may have a substituent(s), preferably among R¹, R² and R³, two or three thereof are each independently a secondary or tertiary aliphatic hydrocarbon group, more preferably among R¹, R² and R³, two are each independently a secondary aliphatic hydrocarbon group, and the remaining one is a tertiary aliphatic hydrocarbon group, further preferably among R¹, R² and R³, two are each independently a secondary $C_{3-6}$ alkyl group, and the remaining one is a tertiary $C_{4-6}$ alkyl group, and more further preferably among R¹, R² and R³, two are i-propyl groups, and the remaining one is a t-butyl group.

In the formula (II), as the other embodiment of R¹, R² and R³, preferably among R¹, R² and R³, two are each independently a secondary aliphatic hydrocarbon group, and the remaining one is a secondary aliphatic hydrocarbon group having a substituent(s) (here, the substituent(s) of the secondary aliphatic hydrocarbon group exist(s) on the carbon atom bonded to the silyl atom.), more preferably among R¹, R² and R³, two are each independently a secondary $C_{3-6}$ alkyl group, and the remaining one is a secondary $C_{3-6}$ alkyl group substituted by a phenyl group(s) (here, the phenyl group(s) which is a substituent of the secondary aliphatic hydrocarbon group exist(s) on the carbon atom bonded to the silyl atom.), and further preferably among R¹, R² and R³, two are i-propyl groups, and the remaining one is a cumyl group.

In the formula (II), as the other embodiment of R¹, R² and R³, preferably among R¹, R² and R³, two are each independently a tertiary aliphatic hydrocarbon group, more preferably among R¹, R² and R³, two are each independently a tertiary $C_{4-6}$ alkyl group, further preferably among R¹, R² and R³, two are t-butyl groups, and the remaining one is an i-butyl group, a benzyl group, an octadecyl group or a cyclohexyl group.

In the formula (II), the total number of the carbon atoms in the R¹R²R³Si group is preferably 10 to 100, more preferably 10 to 40, and further preferably 12 to 26.

As the characteristic feature of the silylcarbamate-based protective group (the protective group of the present invention) having a specific structure used in the present invention, there may be mentioned, for example, the following.

(a) Under the basic conditions (in the presence of a reagent such as an aqueous lithium hydroxide solution, etc.) at which the C-terminal Me group is deprotected, the protective group of the present invention is stable (see Synthetic Example 2, etc., mentioned later).

(b) Under the acidic conditions (in the presence of a reagent such as trifluoromethane-sulfonic acid, etc.) at which the C-terminal t-Bu group is deprotected, the protective group of the present invention is stable (see Synthetic Example 3, etc., mentioned later).

(c) Under the conditions of liquid separating that the C-terminal TMS group is deprotected, the protective group of the present invention is stable (see Synthetic Examples 1 and 4, etc., mentioned later).

(d) It is deprotected in the presence of a fluorine compound (potassium fluoride, ammonium fluoride, etc.).

The terms "N-protected amino acid" and "N-protected peptide" mean an amino acid or peptide in which the amino group at the N-terminal is protected and the carboxy group at the C-terminal is unprotected.

The terms "C-protected amino acid" and "C-protected peptide" mean an amino acid or peptide in which the carboxy group at the C-terminal is protected and the amino group at the N-terminal is unprotected.

The amino acid used in the present invention is an organic compound having both functional groups of the amino group and the carboxy group, preferably α-amino acid, β-amino acid, γ-amino acid or δ-amino acid, more preferably α-amino acid or β-amino acid, and further preferably α-amino acid. Also, when two or more amino groups are present in these amino acids (for example, arginine, lysine, etc.), two or more carboxy groups are present (for example, glutamic acid, aspartic acid, etc.), or a reactive functional group(s) is/are present (for example, cysteine, serine, etc.), the amino acid used in the present invention includes an amino acid in which an amino group, a carboxy group and/or a functional group(s) which do(es) not participate in the formation of a peptide is/are protected and/or modified.

Peptide is a well-known concept to those skilled in the art, and when it is supplemented just in case, the peptide in the present invention refers to a molecule in which an amino acid is used as a monomer and is linked in a chain by a peptide bond, and the amino acids that constitute the peptide used in the present invention are the above-mentioned amino acids.

The steric structure of the α-amino acid is not specifically limited, and it is preferably L-isomer.

The terms "temporary protective group" is a protective group at the terminal side at which the peptide chain is elongated, and mean a protective group that is deprotected before subjecting to peptide elongation reaction (amidation reaction), and in the elongation of the peptide chain to the C-terminal side, a C-terminal protective group is mentioned. As the C-terminal protective group, a protective group of the carboxy group which is generally used in the technical field of the peptide chemistry, etc., can be used, preferably a protective group which is eliminated by the conditions different from elimination of a silylcarbamate-based protective group having a specific structure, and specific examples thereof may be mentioned an alkyl group, an alkenyl group, an alkynyl group, an aralkyl group and a silyl group, preferably a $C_{1-6}$ alkyl group, a $C_{7-10}$ aralkyl group and a tri-$C_{1-6}$ alkylsilyl group, and more preferably a methyl group, an ethyl group, a t-butyl group, a benzyl group and a trimethyl silyl group.

All technical terms and scientific terms used in the present specification have the same meanings as those commonly understood by those skilled in the art to which the present invention belongs. The same or equivalent optional method and material described in the present specification can be used in practice or experiment of the present invention, and preferable methods and materials are described below. All publications and patents referred to in the present specification are incorporated in the present specification by reference, for example, for the purpose of describing and disclosing the constructs and methodologies, which are described in the publications capable of using in connection with the described inventions.

(Specific Explanation of Producing Method of Peptide of the Present Invention)

Hereinafter, each of Steps (i) to (vi) of the producing method of the peptide of the present invention will be explained.

As one embodiment, the production of the peptide of the present invention is constituted by the respective unit steps described as the following Steps (i) to (vi).

As one embodiment, the production of the peptide of the present invention can be carried out by subjecting to all the unit steps described as the following Steps (i) to (vi) or optionally combining these steps.

Incidentally, the specific explanation is explained based on the following.

(a) $R^1$, $R^2$ and $R^3$ in the descriptions of Steps (i) to (vi) have the same meanings as defined above.

(b) The specific conditions of the reaction are not particularly limited as long as the production of the peptide of the present invention is accomplished. Preferred conditions in the respective reactions are appropriately described in detail.

(c) The solvent(s) described in the respective reactions may be used alone or may be used in combination of two or more kinds.

Step (i): Peptide Chain Elongation Step

The present step is a step in which a C-protected amino acid or a C-protected peptide synthesized by using a commercially available product or a silylating agent is condensed to the C-terminal of an N-protected amino acid or an N-protected peptide into which a silylcarbamate-based protective group having a specific structure is introduced at the N-terminal.

Incidentally, the N-protected amino acid or peptide into which the silylcarbamate-based protective group having a specific structure at the N-terminal can be obtained by the methods described in Journal of Organic Chemistry, 1999, vol. 64, pp. 3792-3793, Journal of the American Chemical Society, 2005, vol. 127, pp. 13720-13725 and Reference Synthetic Examples 1, 5 and 7, and a method equivalent thereto.

The present step uses a condensation agent, and carried out under condensing conditions generally used in the technical field of peptide chemistry, etc.

The condensation agent to be used in the present step is not particularly limited, preferably carbodiimide-based condensation agent (for example, N,N'-dicyclohexylcarbodiimide (DCC), N,N'-diisopropylcarbodiimide, 1-ethyl-3-dimethylaminopropylcarbodiimide hydrochloride (EDCI)), a chloroformate-based condensation agent (for example, ethyl chloroformate, isobutyl chloroformate), an acid halide-based condensation agent (for example, pivaloyl chloride), an imidazole-based condensation agent (for example, 1,1'-carbonyldiimidazole (CDI)), a phosphonium-based condensation agent (for example, (benzotriazol-1-yloxy)tripyrrolidinophosphonium hexafluorophosphate (PyBOP (Registered Trademark)), bromotripyrrolidinophosphonium hexafluorophosphate (PyBrop (Registered Trademark))), an uronium-based condensation agent (for example, O-(benzotriazol-1-yl)-N,N,N',N'-tetramethyluronium tetrafluoroborate (TBTU), 1-[bis(dimethylamino)methylene]-5-chloro-1H-benzotriazolium 3-oxide hexafluorophosphate (HCTU), O-benzotriazol-N,N,N',N'-tetramethyluronium hexafluoroborate (HBTU), (1-cyano-2-ethoxy-2-oxoethylideneaminooxy)dimethyl-amino-morpholino-carbenium hexafluorophosphate (COMU)), etc., more preferably carbodiimide-based condensation agent, a chloroformate-based condensation agent, an acid halide-based condensation agent, a phosphonium-based condensation agent or an uronium-based condensation agent, and further preferably isobutyl chloroformate, pivaloyl chloride or (1-cyano-2-ethoxy-2-oxoethylideneaminooxy)dimethylamino-morpholino-carbenium hexafluorophosphate.

An amount of the condensation agent is, based on N-protected amino acid or N-protected peptide, preferably 0.1 equivalent to 20 equivalent, more preferably 1 equivalent to 10 equivalent, and further preferably 1 equivalent to 5 equivalent.

In the present step, an additive(s) and a base(s) may be optionally used as long as it does not prohibit the reaction.

The additive to be used in the present step is not particularly limited, and an example thereof may be mentioned N,N-dimethyl-4-aminopyridine (DMAP), 1-hydroxybenzotriazole (HOBt), ethyl 1-hydroxy-1H-1,2,3-triazol-5-carboxylate (HOCt), 1-hydroxy-7-azabenzotriazole (HOAt), ethyl (hydroxyimino)cyanoacetate (OxymaPure), etc.

An amount of the additives is, based on the N-protected amino acid or N-protected peptide, preferably 0.01 equivalent to 20 equivalent, more preferably 0.2 equivalent to 10 equivalent, and further preferably 1 equivalent to 5 equivalent.

The base to be used in the present step is not particularly limited, and examples thereof may be mentioned an aliphatic amine (for example, triethylamine, N,N-diisopropylethylamine, N-methylmorpholine), an aromatic amine (for example, pyridine), etc. It is preferably an aliphatic amine, more preferably N,N-diisopropyl-ethylamine and N-methylmorpholine.

An amount of the base to be used is, based on the N-protected amino acid or N-protected peptide, preferably 1 equivalent to 50 equivalent, more preferably 1 equivalent to 10 equivalent, and further preferably 1 equivalent to 5 equivalent.

The solvent to be used in the present step is not particularly limited as long as it does not prohibit the reaction, and examples thereof may be mentioned a halogen-containing hydrocarbon solvent (for example, dichloromethane, chloroform), an aromatic hydrocarbon solvent (for example, toluene, xylene), an ether solvent (for example, tetrahydrofuran, 1,4-dioxane, cyclopentylmethyl ether, methyl-t-butyl ether), an amide solvent (for example, N,N-dimethylformamide, etc.), a nitrile solvent (for example, acetonitrile), etc. It is preferably a halogen-containing hydrocarbon solvent, an aromatic hydrocarbon solvent, or an ether solvent, and more preferably toluene, tetrahydrofuran or methyl-t-butyl ether.

An amount of the solvent to be used is, based on the N-protected amino acid or N-protected peptide, preferably 100-fold mass or less, more preferably 1-fold mass to 50-fold mass, and further preferably 5-fold mass to 20-fold mass.

A reaction temperature is not particularly limited, and preferably from −40° C. to the reflux temperature of the reaction mixture, more preferably −20° C. to 50° C., and further preferably −10° C. to 30° C.

A reaction time is not particularly limited, and preferably up to 72 hours from starting the reaction, more preferably 0.1 hour to 48 hours, and further preferably 0.1 to 24 hours.

For confirmation of the progress of the reaction, a method similar to that of a general liquid phase organic synthesis reaction can be applied. That is, the reaction can be traced using thin layer chromatography, high performance liquid chromatography, high performance liquid chromatography/mass analysis (LC/MS), etc.

Step (ii): Deprotection Step of C-Terminal

The present step is a step of removing the C-terminal protective group of the peptide obtained in the above-mentioned Step (i).

The deprotection conditions are appropriately selected depending on the kind of the C-terminal protective group, but it is preferable to deprotect under the conditions different from the elimination of the silylcarbamate-based protective group having a specific structure. When the C-terminal protective group is a $C_{1-6}$ alkyl group, it is carried out by treating with a base or an acid (for example, in the case of a methyl group, it is carried out by treating with a base, and in the case of a t-butyl group, it is carried out by treating with an acid), when it is a $C_{7-10}$ aralkyl group (for example, a benzyl group, etc.), it is carried out by subjecting to hydrogenation in the presence of a metal catalyst, and when it is a tri-$C_{1-6}$ alkylsilyl group (for example, a trimethylsilyl group, a triethylsilyl group, a t-butyldimethylsilyl group, etc.), it is carried out by treating with water (neutral, an acidic or basic aqueous solution, etc.).

As the base used in the present step, there may be mentioned sodium hydroxide, potassium hydroxide, lithium hydroxide, potassium hydrogen carbonate, potassium carbonate, dimethylamine, diethylamine, piperidine, hydrazine, etc.

As the acid used in the present step, there may be mentioned hydrochloric acid, sulfuric acid, trifluoroacetic acid, trifluoromethanesulfonic acid, etc.

As the metal catalyst used in the reaction, there may be mentioned, for example, palladium carbon powder, platinum carbon powder, ruthenium carbon powder, alumina powder, etc.

The aqueous solution to be used in the present step is not particularly limited, and as the acidic aqueous solution, there may be mentioned hydrochloric acid, sulfuric acid, an aqueous acetic acid solution, an aqueous phosphoric acid solution, an aqueous citric acid solution, an aqueous ammonium chloride solution, etc. As the basic aqueous solution, there may be mentioned an aqueous sodium hydrogen carbonate solution, an aqueous potassium hydrogen carbonate solution, an aqueous sodium carbonate solution, an aqueous potassium carbonate solution, aqueous ammonia, etc.

The solvent to be used in the present step is not particularly limited as long as it does not prohibit the reaction, and examples thereof may be mentioned an alcohol solvent (for example, methanol, ethanol, 2-propanol, 2,2,2-trifluoroethanol), a halogen-containing hydrocarbon solvent (for example, dichloromethane, chloroform), an aromatic hydrocarbon solvent (for example, toluene, xylene), an ether solvent (for example, tetrahydrofuran, 1,4-dioxane, cyclopentyl methyl ether, methyl-t-butyl ether), an amide solvent (for example, N,N-dimethylformamide), a nitrile solvent (for example, acetonitrile), etc. It is preferably an alcohol solvent, a halogen-containing hydrocarbon solvent, or an ether solvent, and more preferably toluene, tetrahydrofuran or methyl-t-butyl ether.

Step (iii): Purification Step

The present step is a step of purifying the peptide obtained in the above-mentioned Step (ii) by a liquid separating operation.

In the liquid separating operation, impurities can be removed by washing a good solvent in which the peptide is dissolved with water, or an acidic and/or basic aqueous solution depending on the target peptide or impurities that can be contained.

The acidic aqueous solution used in the present step is not particularly limited, and an example thereof may be mentioned hydrochloric acid, sulfuric acid, an aqueous acetic acid solution, an aqueous phosphoric acid solution, an aqueous citric acid solution, an aqueous ammonium chloride solution, etc. It is preferably hydrochloric acid, an aqueous phosphoric acid solution, an aqueous citric acid solution or an aqueous ammonium chloride solution.

The basic aqueous solution used in the present step is not particularly limited, and an example thereof may be mentioned an aqueous sodium hydrogen carbonate solution, an aqueous potassium hydrogen carbonate solution, an aqueous sodium carbonate solution, an aqueous potassium carbonate solution, aqueous ammonia, etc. It is preferably an aqueous potassium carbonate solution and aqueous ammonia.

Also, in the production method of the peptide of the present invention, the peptide chain can be further elongated by repeating the following Steps (iv) to (vi) a desired number of times with respect to the peptide obtained in the step (ii).

(iv) a step of condensing a C-protected amino acid or a C-protected peptide to the C-terminal of the peptide obtained in the purification step, and (v) a step of removing the temporary protective group of the C-terminal of the peptide obtained in the above-mentioned Step (iv), (vi) a step of liquid-separating the peptide obtained in the above-mentioned Step (v). Each can be carried out by the same operations as in the above-mentioned Steps (i) to (iii).

The present step may be carried out on the peptide obtained in the peptide chain elongation step of the above-mentioned Step (i) or (iv).

In the producing method of the peptide of the present invention, it is also possible to appropriately omit the purification step of Step (ii) or Step (v) within the range which does not affect the reaction in the next step.

Step (Vii): Deprotection Step of N-Terminal

The present step is a step of removing the N-terminal protective group from the peptide obtained in the above-mentioned Steps (ii) to (vi).

The present step is carried out by reacting a reagent such as a fluorine compound, etc., in a solvent which does not affect the reaction.

As the solvent which does not exert any effect to the reaction, there may be mentioned, for example, an alcohol solvent, a halogen-containing hydrocarbon solvent, an aromatic hydrocarbon solvent, an ether solvent, an amide solvent, a nitrile solvent, etc. It is preferably an alcohol solvent, an ether solvent, an amide solvent or a nitrile solvent, and more preferably methanol, tetrahydrofuran, N-methylpyrrolidone or acetonitrile.

The fluorine compound used in the reaction may be mentioned, for example, hydrogen fluoride-amine salt (for example, tetrabutylammonium fluoride, ammonium fluoride, hydrogen fluoride-pyridine complex, hydrogen fluoride-triethylamine complex), hydrogen fluoride-metal salt (for example, potassium fluoride, cesium fluoride, calcium fluoride). It is preferably tetrabutylammonium fluoride, ammonium fluoride or potassium fluoride, and more preferably ammonium fluoride or potassium fluoride.

When the present reaction is carried out, a reaction temperature is generally any temperature in the range of −20° C. to the boiling point of the solvent used, preferably 0° C. to 60° C., and more preferably 10° C. to 40° C. Also, a reaction time is generally 1 to 24 hours, and preferably 1 to 5 hours.

In the respective reactions, when the reaction substrate has a hydroxy group, a mercapto group, an amino group, a carboxy group or carbonyl group (in particular, when the side chain of the amino acid or peptide has a functional group), a protective group such as that generally used in peptide chemistry, etc., may be introduced into these groups, and by removing the protective group after the reaction depending on necessity, the target compound can be obtained.

Protection and deprotection can be practiced by subjecting to protection and deprotection reaction (for example, see Protective Groups in Organic Synthesis, Fourth edition, written by T. W. Greene, John Wiley & Sons Inc., 2006, etc.) using a generally known protective group.

EXAMPLES

Hereinafter, the present invention will be explained in more detail by referring to Reference Synthetic Examples and Synthetic Examples, but the present invention is not limited to these Examples.

In the present specification, when the amino acid, etc., are indicated as an abbreviation, each indication is based on the abbreviation by IUPAC-IUB Commission on Biochemical Nomenclature or the conventional abbreviation in this field of the art.

Incidentally, in Synthetic Examples, "M" means mol/L.

The proton nuclear magnetic resonance ($^1$H-NMR) in Examples was measured by, unless otherwise specifically mentioned, JNM-ECP300 manufactured by JEOL, Ltd., or JNM-ECX300 manufactured by JEOL, Ltd., or, Ascend™500 manufactured by Bruker Co., in deuterated chloroform or deuterated dimethyl sulfoxide solvent, and the chemical shift was shown by the δ value (ppm) when tetramethylsilane was used as the internal standard (0.0 ppm).

In the description of the NMR spectrum, "s" means singlet, "d" means doublet, "t" means triplet, "q" means quartet, "sep" means septet, "dt" means doublet of triplet, "m" means multiplet, "br" means broad, "J" means coupling constant, "Hz" means helz, and "CDCl$_3$" means deuterated chloroform.

High performance liquid chromatography/mass analysis was measured using, unless otherwise specifically mentioned, either of ACQUITY UPLC H-Class/QDa manufactured by Waters Corporation, ACQUITY UPLC H-Class/SQD2 manufactured by Waters Corporation or LC-20AD/Triple Tof5600 manufactured by Shimadzu Corporation.

In the description of high performance liquid chromatography/mass analysis, ESI+ means a positive mode of the electrospray ionization method, M+H means a proton adduct and M+Na means a sodium adduct.

In the description of high performance liquid chromatography/mass analysis, ESI− means a negative mode of the electrospray ionization method, and M−H means a proton deficient.

In purification by silica gel column chromatography, unless otherwise specifically mentioned, either of Hi-Flash column manufactured by Yamazen Corporation, SNAP Ultra Silica Cartridge manufactured by Biotage AG, silica gel 60 manufactured by Merck or PSQ60B manufactured by Fuji Silysia Chemical Ltd., was used.

Reference Synthetic Example 1: Synthesis of Tsoc-Phe-OH

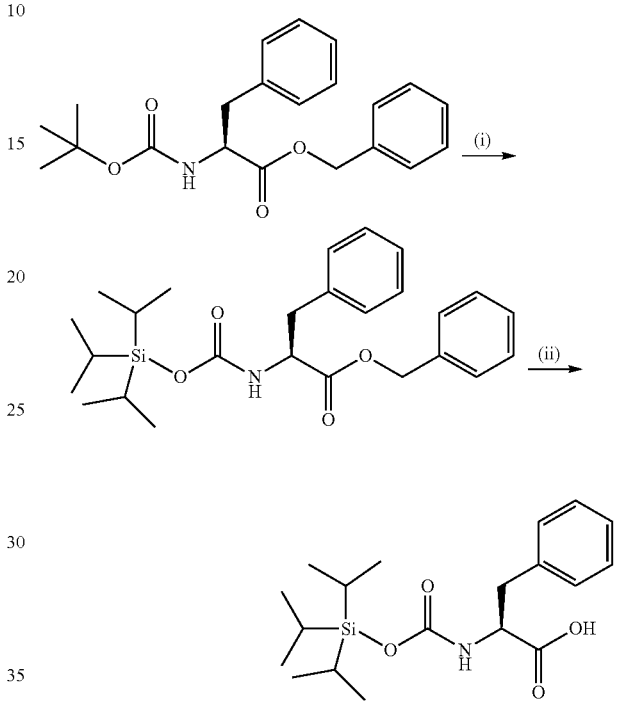

(i) Boc-Phe-OBn (1.49 g, 4.22 mmol) and lutidine (0.68 g, 6.3 mmol) were mixed with acetonitrile (15 mL), and triisopropylsilyl trifluoromethanesulfonate (1.42 g, 4.63 mmol) was added thereto at 0° C. and the mixture was stirred for 3 hours. To the mixture were added lutidine (0.68 g, 6.3 mmol) and triisopropyl silyl trifluoromethanesulfonate (1.42 g, 4.63 mmol) at 0° C., and the temperature of the mixture was raised to room temperature and stirred for 20 hours. The obtained reaction mixture was diluted with t-butyl methyl ether (45 mL), and washed successively with a saturated aqueous sodium hydrogen carbonate solution (15 mL), saturated aqueous ammonium chloride solution (15 mL) and water (15 mL) in this order. After concentrating the obtained organic layer, the residue was purified by silica gel column chromatography to obtain Tsoc-Phe-OBn (1.56 g, Yield: 82%) as a colorless liquid.

$^1$H-NMR (CDCl$_3$)

δ ppm: 1.04-1.06 (18H, m), 1.27 (3H, sep, J=7.8 Hz), 3.04-3.18 (2H, m), 4.63-4.50 (1H, m), 5.09-5.21 (3H, m), 7.02-7.63 (10H, m)

MASS (ESI+) m/z; (M+H)+456.37

(ii) Tsoc-Phe-OBn (0.383 g, 0.840 mmol) was mixed with ethyl acetate (8.0 mL), and after adding 10 wt % Pd—C (39.9 mg, 0.037 mmol) thereto, the mixture was stirred under a hydrogen gas atmosphere at room temperature for 1 hour. The reaction mixture was filtered and the obtained filtrate was concentrated to obtain Tsoc-Phe-OH (0.31 g, Yield: 101%).

¹H-NMR (CDCl₃)

δ ppm: 1.05 (18H, d, J=7.5 Hz), 1.26 (3H, Sep, 7.5 Hz), 3.06-3.27 (2H, m), 4.60-4.66 (1H, m), 5.13 (2H, d, 7.5 Hz), 7.18-7.33 (5H, m)

MASS (ESI+) m/z; (M+H)+366.32

Reference Synthetic Example 2: Synthesis of Tsoc-Phe-Phe-OH

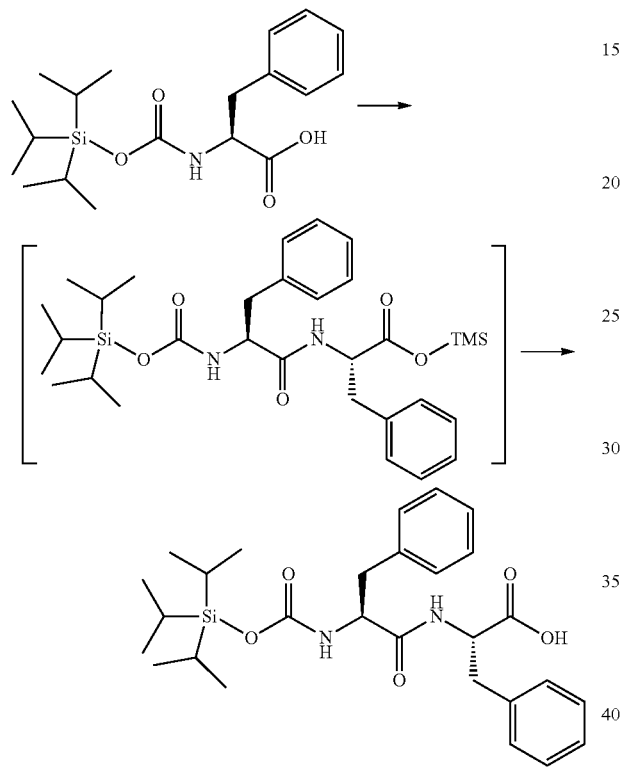

Tsoc-Phe-OH (0.222 g, 0.608 mmol) and N-methylmorpholine (0.064 g, 0.63 mmol) were mixed with tetrahydrofuran (4.0 mL), and isobutyl chloroformate (0.082 g, 0.60 mmol) was added thereto at 0° C. and the mixture was stirred for 15 minutes. To the solution was added a solution separately prepared by mixing H-Phe-OH (0.109 g, 0.66 mmol), N,O-bis(trimethylsilyl)acetamide (0.268 g, 1.32 mmol) and tetrahydrofuran (1.0 mL) and stirring at 55° C. for 1 hour, and the mixture was stirred at 0° C. for 2 hours so that disappearance of the starting materials was confirmed. The obtained reaction mixture was diluted with t-butyl methyl ether (4.0 mL), and successively washed with a 10 wt % aqueous potassium carbonate solution (2.0 mL), a 20 wt % aqueous ammonium chloride solution (2.0 mL) and a saturated aqueous sodium chloride solution (4.0 mL). The obtained organic layer was concentrated and purified by silica gel column chromatography to obtain Tsoc-Phe-Phe-OH (0.089 g, Yield: 29%) as a white solid.

¹H-NMR (CDCl₃)

δ ppm: 0.90-1.19 (18H, m), 1.21-1.32 (3H, m), 2.79-3.21 (4H, m), 4.37 (1H, br), 4.58 (1H, br), 5.66 (1H, br), 5.87 (1H, br), 7.09 (10H, br)

MASS (ESI+) m/z; (M+H)+513.35

Reference Synthetic Example 3: Synthesis of Tsoc-Phe-Phe-OH

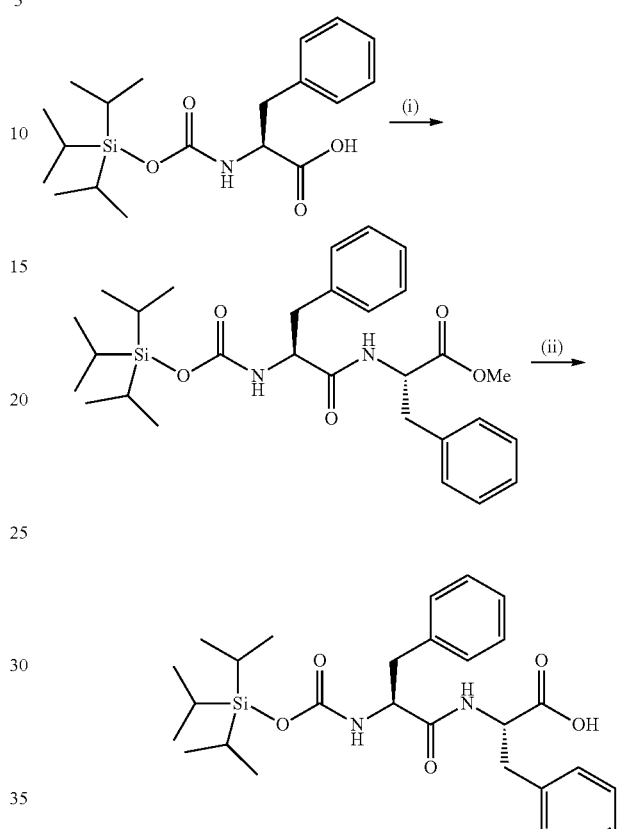

(i) Tsoc-Phe-OH (0.298 g, 0.815 mmol) and N-methylmorpholine (0.186 g, 1.84 mmol) were mixed with ethyl acetate (8.0 mL), and isobutyl chloroformate (0.126 g, 0.92 mmol) was added thereto at −30° C. To the solution was added H-Phe-OMe hydrochloride (0.201 g, 0.93 mmol), and then, the mixture was stirred at the same temperature for 30 minutes. The temperature of the reaction mixture was raised to room temperature, and after stirring the mixture for 1 hour, it was successively washed with 5 wt % an aqueous sodium hydrogen carbonate solution (3.0 mL, twice) and water (3.0 mL). The obtained organic layer was concentrated and purified by silica gel column chromatography to obtain Tsoc-Phe-Phe-OMe (0.436 g, Yield: 102%) as colorless oil.

¹H-NMR (CDCl₃)

δ ppm: 0.90 (1H, d, J=6.9 Hz), 1.02-1.06 (18H, m), 1.26 (3H, Sep, J=7.5 Hz), 2.97-3.10 (4H, m), 3.65 (3H, s), 4.30-4.38 (1H, m), 4.71-4.78 (1H, m), 5.21 (1H, d, J=7.8 Hz), 6.16 (1H, d, J=7.2 Hz), 6.97-7.29 (10H, m)

MASS (ESI+) m/z; (M+H)+527.33

(ii) Tsoc-Phe-Phe-OMe (0.078 g, 0.15 mmol) was mixed with methanol (1.6 mL), and 5 wt % aqueous lithium hydroxide solution (0.085 g, 0.18 mmol) was added thereto and the mixture was stirred at room temperature for 10 minutes. When the reaction mixture was analyzed by LC-MS, Tsoc-Phe-Phe-OMe was decomposed and no Tsoc-Phe-Phe-OH was formed.

Reference Synthetic Example 4: Synthesis of Tsoc-Phe-Phe-OH

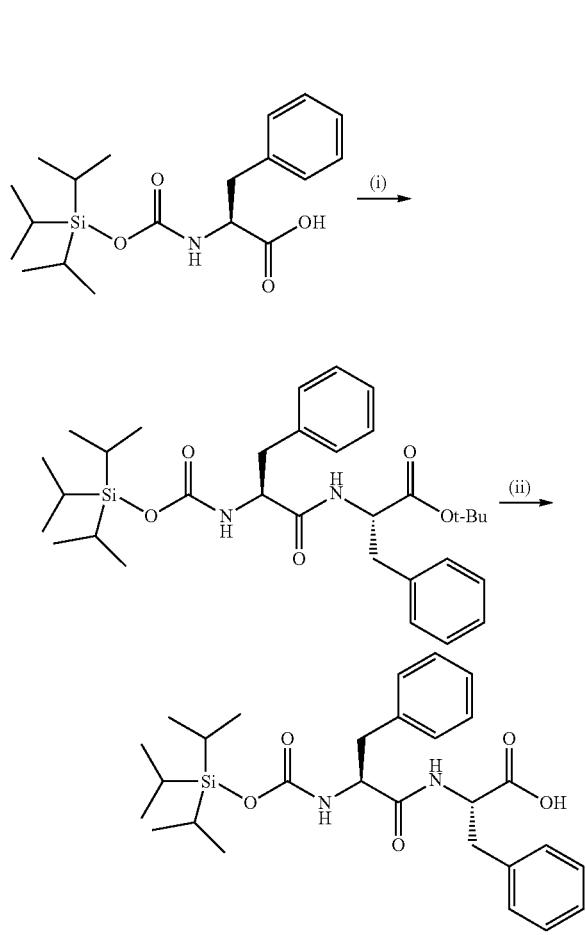

(i) Tsoc-Phe-OH (0.279 g, 0.764 mmol), N-methylmorpholine (0.162 g, 1.60 mmol) were mixed with ethyl acetate (5.6 mL), and isobutyl chloroformate (0.110 g, 0.80 mmol) was added thereto at −10° C. To the solution was added H-Phe-O(t-Bu) hydrochloride (0.207 g, 0.80 mmol), and then, the mixture was stirred at the same temperature for 45 minutes. The obtained reaction mixture was successively washed with 5 wt % an aqueous sodium hydrogen carbonate solution (5.6 mL, twice) and water (5.6 mL). The obtained organic layer was concentrated and purified by silica gel column chromatography to obtain Tsoc-Phe-Phe-O(t-Bu) (0.294 g, Yield: 68%) as a white solid.

$^1$H-NMR (CDCl$_3$)

δ ppm: 1.05 (18H, d, J=7.2 Hz), 1.27 (3H, Sep, J=7.2 Hz), 1.35 (9H, s), 3.01-3.06 (4H, m), 4.31-4.38 (1H, m), 4.57-4.63 (1H, m), 5.22 (1H, d, J=8.1 Hz), 6.15 (1H, d, J=7.5 Hz), 7.03-7.29 (10H, m)

MASS (ESI+) m/z; (M+H)+569.38

(ii) Tsoc-Phe-Phe-O(t-Bu) (0.10 g, 0.18 mmol) was mixed with methylene chloride (2.0 mL), and trifluoroacetic acid (0.80 g, 7.0 mmol) was added thereto and the mixture was stirred for 2 hours and 30 minutes. When the reaction mixture was analyzed by LC-MS, Tsoc-Phe-Phe-O(t-Bu) was decomposed, and no Tsoc-Phe-Phe-OH was formed.

Reference Synthetic Example 5: Synthesis of BIBSoc-Phe-OH

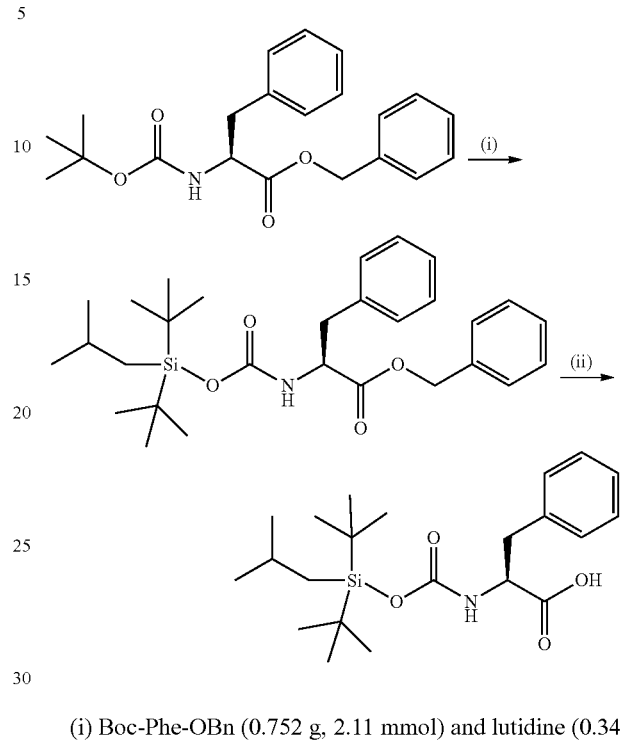

(i) Boc-Phe-OBn (0.752 g, 2.11 mmol) and lutidine (0.34 g, 3.16 mmol) were mixed with acetonitrile (7.5 mL), di-t-butylisobutylsilyl trifluoromethanesulfonate (0.81 g, 2.32 mmol) was added thereto at 0° C. and the mixture was stirred for 2 hours. To the mixture were added lutidine (0.11 g, 1.1 mmol) and di-t-butylisobutylsilyl trifluoro-methanesulfonate (0.27 g, 0.77 mmol) at 0° C., and the temperature of the mixture was raised to room temperature and it was stirred for 16 hours. The obtained reaction mixture was diluted with t-butyl methyl ether (23 mL), and successively washed with a saturated aqueous sodium hydrogen carbonate solution (7.5 mL), a saturated aqueous ammonium chloride solution (7.5 mL) and water (7.5 mL) in this order. The obtained organic layer was concentrated and purified by silica gel column chromatography to obtain BIBSoc-Phe-OBn (0.83 g, Yield: 79%) as a colorless liquid.

$^1$H-NMR (CDCl$_3$)

δ ppm: 0.83 (2H, d, J=6.9 Hz), 0.94 (6H, d, J=6.6 Hz), 1.03 (18H, m), 1.99 (1H, br Sep, J=6.9 Hz), 3.03-3.17 (2H, m), 4.67 (1H, dt, J=8.4 Hz, 6.0 Hz), 5.08-5.19 (3H, m), 7.01-7.35 (10H, m)

MASS (ESI+) m/z; (M+H)+498.42

(ii) BIBSoc-Phe-OBn (0.330 g, 0.69 mmol) was mixed with ethyl acetate (5.0 mL), and after adding 10 wt % Pd—C (38.9 mg, 0.037 mmol) thereto, the mixture was stirred under a hydrogen gas atmosphere at room temperature for 1 hours and 30 minutes. The reaction mixture was filtered and the obtained filtrate was concentrated to obtain BIBSoc-Phe-OH (0.250 g, Yield: 92%).

$^1$H-NMR (CDCl$_3$)

δ ppm: 0.83 (2H, d, J=6.9 Hz), 0.94 (6H, br d, J=6.6 Hz), 1.03 (18H, m), 1.99 (1H, Sep, J=6.6 Hz), 3.06-3.26 (2H, m), 4.60-4.66 (1H, m), 5.04 (1H, d, J=7.8 Hz), 7.16-7.32 (5H, m)

MASS (ESI+) m/z; (M+H)+408.33

Synthetic Example 1: Synthesis of BIBSoc-Phe-Phe-OH

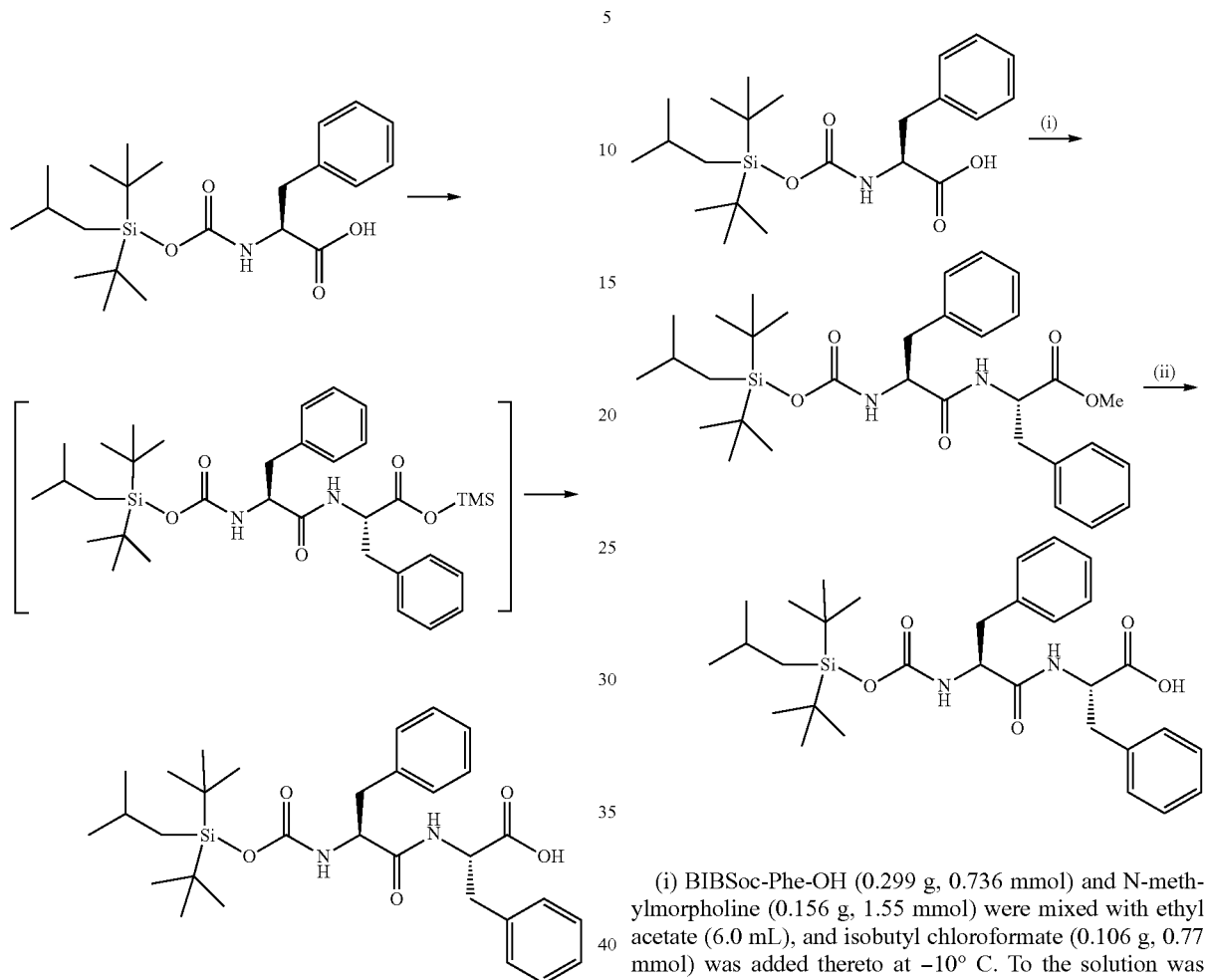

BIBSoc-Phe-OH (0.151 g, 0.368 mmol) and N-methylmorpholine (0.043 g, 0.42 mmol) were mixed with tetrahydrofuran (3.0 mL), and isobutyl chloroformate (0.055 g, 0.40 mmol) was added thereto at 0° C. and the mixture was stirred for 15 minutes. To the solution was added a solution separately prepared by mixing H-Phe-OH (0.074 g, 0.44 mmol), N,O-bis(trimethylsilyl)acetamide (0.18 g, 0.88 mmol) and tetrahydrofuran (0.75 mL) and stirring at 55° C. for 1 hour, and the mixture was further stirred while maintaining to 0° C. for 2 hours. The obtained reaction mixture was diluted with t-butyl methyl ether (3.0 mL), and successively washed with a 10 wt % aqueous potassium carbonate solution (1.5 mL), a 20 wt % aqueous ammonium chloride solution (1.5 mL) and a saturated aqueous sodium chloride solution (1.5 mL). The obtained organic layer was concentrated and purified by silica gel column chromatography to obtain BIBSoc-Phe-Phe-OH (0.174 g, Yield: 85%) as a white solid.

$^1$H-NMR (CDCl$_3$)

δ ppm: 0.76-1.04 (27H, m), 2.85-3.30 (4H, m), 4.36 (1H, br), 4.60 (1H, br), 6.91-7.20 (10H, br)

MASS (ESI+) m/z; (M+H)+555.38

Synthetic Example 2: Synthesis of BIBSoc-Phe-Phe-OH (i) BIBSoc-Phe-OH (0.299 g, 0.736 mmol) and N-methylmorpholine (0.156 g, 1.55 mmol) were mixed with ethyl acetate (6.0 mL), and isobutyl chloroformate (0.106 g, 0.77 mmol) was added thereto at −10° C. To the solution was added H-Phe-OMe hydrochloride (0.199 g, 0.92 mmol), and then, the mixture was stirred at the same temperature for 30 minutes. The obtained reaction mixture was successively washed with a 5 wt % an aqueous sodium hydrogen carbonate solution (6.0 mL, twice) and water (6.0 mL). The obtained organic layer was concentrated and purified by silica gel column chromatography to obtain BIBSoc-Phe-Phe-OMe (0.420 g, Yield: 101%) as a white solid.

$^1$H-NMR (CDCl$_3$)

δ ppm: 0.81 (2H, d, J=6.3 Hz), 0.89-0.95 (6H, m), 1.02 (18H, d, J=1.8 Hz), 1.98 (1H, Sep, J=6.6 Hz), 2.97-3.09 (4H, m), 3.65 (3H, s), 4.31-4.39 (1H, m), 4.71-4.78 (1H, m), 5.13 (1H, d, J=8.1 Hz), 6.13 (1H, d, J=7.8 Hz), 6.94-7.29 (10H, m)

MASS (ESI+) m/z; (M+H)+569.38

(ii) BIBSoc-Phe-Phe-OMe (0.10 g, 0.18 mmol) was mixed with methanol (2.0 mL), and 5 wt % aqueous lithium hydroxide solution (0.10 g, 0.21 mmol) was added thereto and the mixture was stirred for 23 hours. To the obtained reaction mixture was added 4 wt % hydrochloric acid (1.0 mL) and the mixture was quenched, ethyl acetate (2.0 mL) and water (2.0 mL) were added thereto and the liquids were separated. The obtained organic layer was concentrated and purified by silica gel column chromatography to obtain BIBSoc-Phe-Phe-OH (0.082 g, Yield: 85%) as a white solid.

Synthetic Example 3: Synthesis of BIBSoc-Phe-Phe-OH

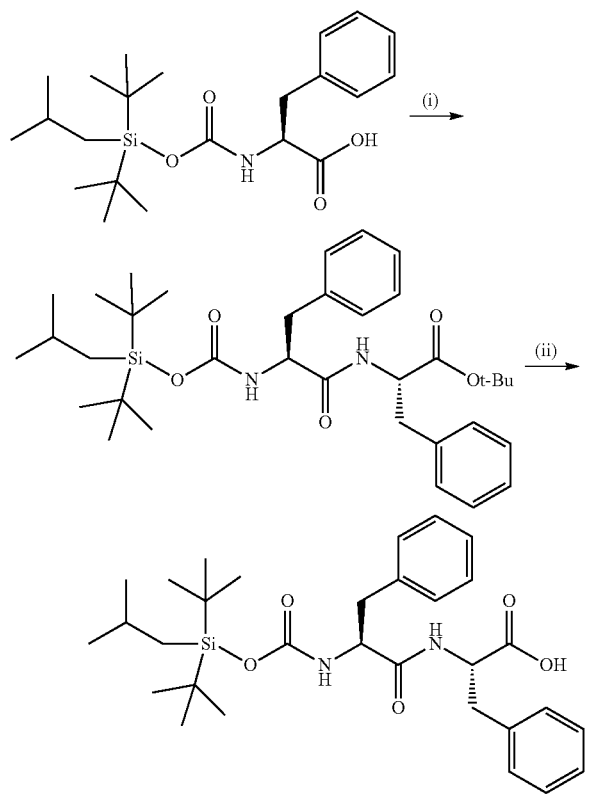

(i) BIBSoc-Phe-OH (0.159 g, 0.393 mmol) and N-methylmorpholine (0.083 g, 0.82 mmol) were mixed with ethyl acetate (3.2 mL), and isobutyl chloroformate (0.056 g, 0.41 mmol) was added thereto at −10° C. To the solution was added H-Phe-O(t-Bu) hydrochloride (0.109 g, 0.42 mmol), and then, the mixture was stirred at the same temperature for 45 minutes. The obtained reaction mixture was successively washed with a 5 wt % aqueous sodium hydrogen carbonate solution (3.2 mL, twice) and water (3.2 mL). The obtained organic layer was concentrated and purified by silica gel column chromatography to obtain BIBSoc-Phe-Phe-O(t-Bu) (0.239 g, Yield: 100%) as a white solid.

$^1$H-NMR (CDCl$_3$)

δ ppm: 0.82 (2H, d, J=5.7 Hz), 0.90-0.96 (6H, m), 1.02 (18H, d, J=1.8 Hz), 1.35 (9H, s), 1.99 (1H, Sep, J=6.6 Hz), 3.00-3.05 (4H, m), 4.31-4.38 (1H, m), 4.56-4.63 (1H, m), 5.17 (1H, d, J=8.1 Hz), 6.19 (1H, d, J=7.5 Hz), 7.03-7.28 (10H, m)

MASS (ESI+) m/z; (M+H)+611.45

(ii) BIBSoc-Phe-Phe-O(t-Bu) (0.092 g, 0.15 mmol) was mixed with methylene chloride (1.9 mL), and trifluoroacetic acid (0.69 g, 6.1 mmol) was added thereto and the mixture was stirred for 4 hours and 30 minutes. To the obtained reaction mixture was added a 10 wt % aqueous sodium carbonate solution (2.0 mL) and the mixture was quenched, and the liquids were separated. The obtained organic layer was concentrated and purified by silica gel column chromatography to obtain BIBSoc-Phe-Phe-OH (0.079 g, Yield: 94%) as a white solid.

Reference Synthetic Example 6: Synthesis of IPBS-OTf

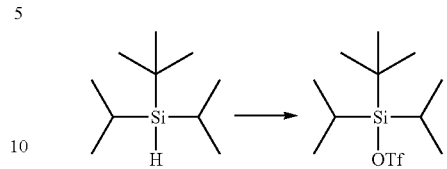

Di-i-propyl-t-butylsilane (0.300 g, 1.74 mmol) was mixed with methylene chloride (10.0 g), and after adding trifluoromethanesulfonic acid (0.160 g, 1.07 mmol) dropwise under ice-cooling, the temperature of the mixture was raised to room temperature and the mixture was stirred for 1 hour. The formed di-i-propyl-t-butylsilyl triflate was used in the next reaction as a methylene chloride solution without isolation.

Reference Synthetic Example 7: Synthesis of IPBSoc-Phe-OH

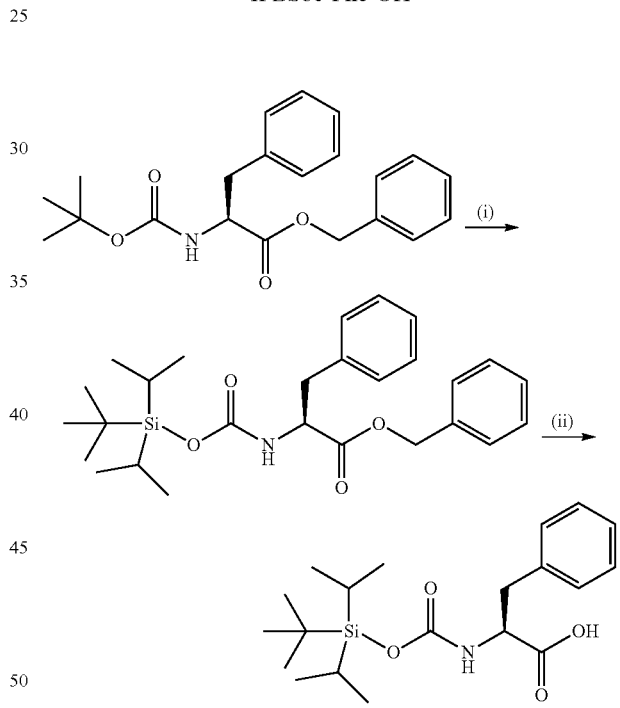

(i) Boc-Phe-OBn (0.500 g, 1.41 mmol) and lutidine (0.326 g, 3.04 mmol) were mixed with acetonitrile (5.0 mL), and a methylene chloride solution of di-i-propyl-t-butylsilyl trifluoromethanesulfonate (1.74 mmol) was added thereto at 0° C., and then, the mixture was stirred at room temperature for 2 hours. A methylene chloride solution of di-i-propyl-t-butylsilyl trifluoromethanesulfonate (0.42 mmol) was further added at 0° C., and the mixture was stirred at room temperature for 16 hours. The obtained reaction mixture was diluted with t-butyl methyl ether (10 mL), and successively washed with a saturated aqueous sodium hydrogen carbonate solution (10 mL), a saturated aqueous ammonium chloride solution (10 mL) and water (10 mL) in this order. The obtained organic layer was concentrated and purified by silica gel column chromatography to obtain IPBSoc-Phe-OBn (0.618 g, Yield: 94%) as a colorless liquid.

MASS (ESI+) m/z; (M+H)+470.26

(ii) IPBSoc-Phe-OBn (0.161 g, 0.341 mmol) was mixed with ethyl acetate (3.2 mL), and after adding 10 wt % Pd—C (20.4 mg, 0.019 mmol) thereto, the mixture was stirred under a hydrogen gas atmosphere at room temperature for 1 hour. The reaction mixture was filtered and the obtained filtrate was concentrated to obtain IPBSoc-Phe-OH (0.138 g, Yield: 107%).

$^1$H-NMR (CDCl$_3$)

δ ppm: 1.02 (9H, s), 1.10-1.12 (12H, m), 1.42 (2H, Sep, 7.4 Hz), 3.06-3.27 (2H, m), 4.60-4.66 (1H, m), 5.13 (2H, d, J=8.1 Hz), 7.17-7.32 (5H, m)

MASS (ESI+) m/z; (M+H)+380.30

Synthetic Example 4: Synthesis of IPBSoc-Phe-Phe-OH

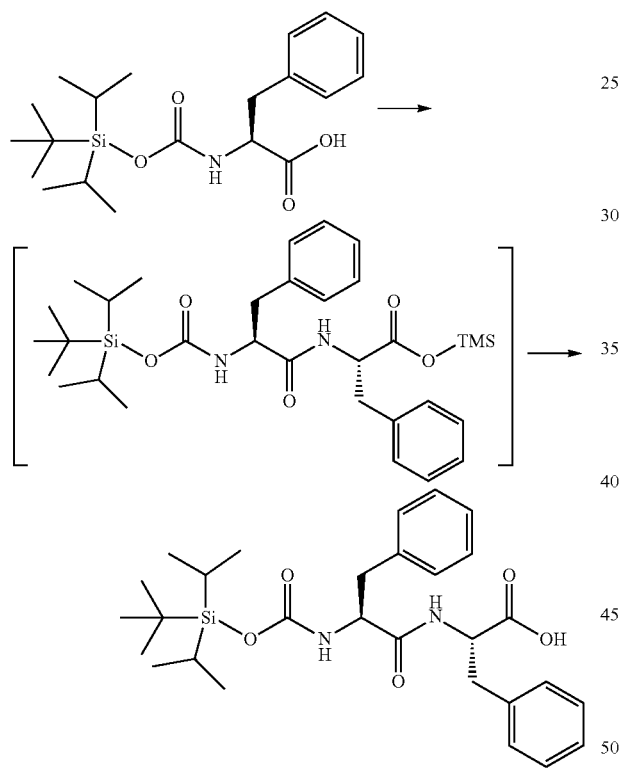

IPBSoc-Phe-OH (0.138 g, 0.365 mmol) and N-methylmorpholine (0.040 g, 0.39 mmol) were mixed with tetrahydrofuran (2.6 mL), and isobutyl chloroformate (0.051 g, 0.37 mmol) was added thereto at 0° C. and the mixture was stirred for 15 minutes. To the solution was mixed with a solution separately prepared by mixing H-Phe-OH (0.068 g, 0.41 mmol), N,O-bis(trimethylsilyl)acetamide (0.17 g, 0.82 mmol) and tetrahydrofuran (0.7 mL) and stirring at 55° C. for 1 hour, and the mixture was further stirred while maintaining to 0° C. for 2 hours. The obtained reaction mixture was diluted with t-butyl methyl ether (2.6 mL), and successively washed with a 10 wt % aqueous potassium carbonate solution (1.3 mL), a 20 wt % aqueous ammonium chloride solution (1.3 mL) and a saturated aqueous sodium chloride solution (2.6 mL). The obtained organic layer was concentrated and purified by silica gel column chromatography to obtain IPBSoc-Phe-Phe-OH (0.152 g, Yield: 79%) as a white solid.

$^1$H-NMR (CDCl$_3$)

δ ppm: 0.97-1.02 (21H, m), 1.36 (2H, br), 2.80-3.21 (4H, m), 3.79 (1H, br), 4.38-4.61 (1H, m), 7.15 (10H, br)

MASS (ESI+) m/z; (M+H)+527.35

Reference Synthetic Example 8: Synthesis of IPCS-OTf

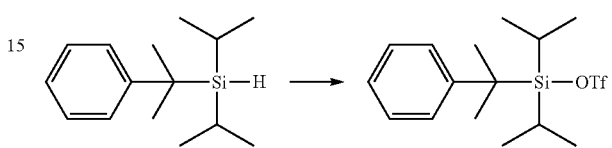

Di-i-propylcumylsilane (0.48 g, 2.0 mmol) was mixed with methylene chloride (2.5 g), and after adding trifluoromethanesulfonic acid (0.38 g, 2.5 mmol) dropwise under ice-cooling, and the temperature of the mixture was raised to room temperature and the mixture was stirred for 0.5 hour. The formed di-i-propylcumylsilyl triflate was used in the next reaction as a methylene chloride solution without isolation.

Reference Synthetic Example 9: Synthesis of IPCSoc-Phe-OH

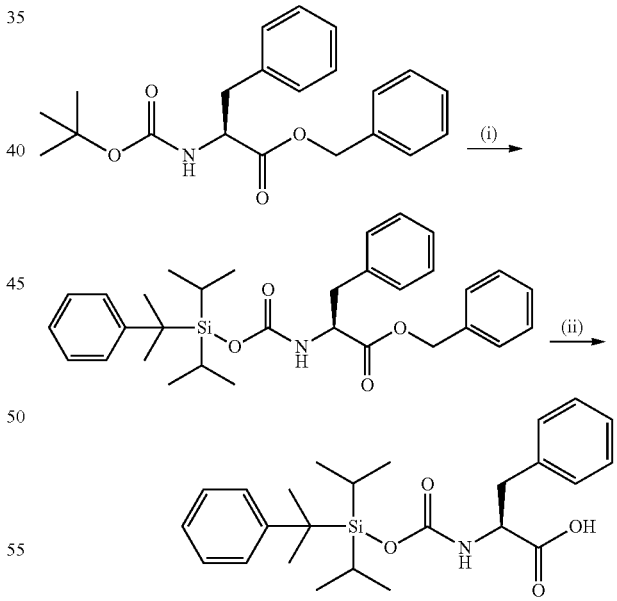

(i) Boc-Phe-OBn (0.37 g, 1.0 mmol) and lutidine (0.36 g, 3.4 mmol) were mixed with acetonitrile (5.0 g), and a methylene chloride solution of di-i-propylcumylsilyl triflate (2.0 mmol) was added thereto at 0° C., and then, the mixture was stirred at room temperature for 3 hours. The obtained reaction mixture was diluted with ethyl acetate, and successively washed with a saturated aqueous sodium hydrogen carbonate solution, a saturated aqueous ammonium chloride solution and saturated brine in this order. The obtained organic layer was concentrated and purified by silica gel column chromatography to obtain IPCSoc-Phe-OBn (0.518 g, Yield: 92%) as a colorless oily product.

MASS (ESI+) m/z; (M+H)+532.29

(ii) IPCSoc-Phe-OBn (0.20 g, 0.38 mmol) was mixed with ethyl acetate (4.0 g), and after adding 10 wt % Pd—C (0.03 g), the mixture was stirred under a hydrogen gas atmosphere at room temperature for 5 hours. After filtrating the reaction mixture, the obtained filtrate was concentrated to obtain IPCSoc-Phe-OH (0.17 g, Yield: 100%).

MASS (ESI+) m/z; (M+H)+442.24

Synthetic Example 5: Synthesis of IPCSoc-Phe-Lys(Boc)-OH

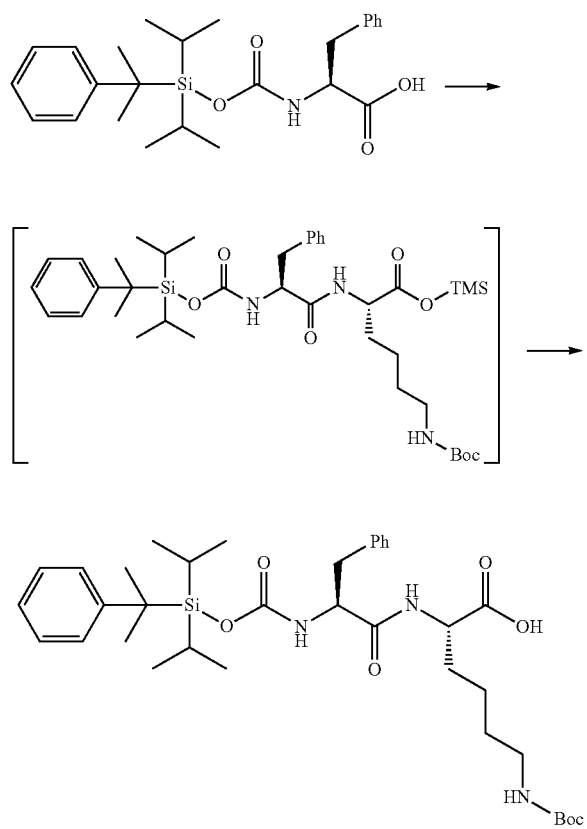

IPCSoc-Phe-OH (0.20 g, 0.46 mmol) and N-methylmorpholine (0.06 g, 0.59 mmol) were mixed with tetrahydrofuran (2.0 g), isobutyl chloroformate (0.08 g, 0.58 mmol) was added thereto at 0° C. and the mixture was stirred for 5 minutes. To the solution was added a solution separately prepared by mixing H-Lys(Boc)-OH (0.15 g, 0.61 mmol), N,O-bis(trimethylsilyl)acetamide (0.25 g, 1.2 mmol) and tetrahydrofuran (1.3 g) and stirring at 55° C. for 0.5 hour, and the mixture was further stirred while maintaining to 0° C. for 2 hours. The obtained reaction mixture was diluted with ethyl acetate, and successively washed with a saturated aqueous sodium hydrogen carbonate solution, a saturated aqueous ammonium chloride solution and a saturated aqueous sodium chloride solution. The obtained organic layer was concentrated to obtain IPCSoc-Phe-Lys(Boc)-OH (0.32 g, Yield: 103%) as a white solid.

MASS (ESI+) m/z; (M+H)+670.39

Synthetic Example 6: Synthesis of IPCSoc-Phe-Lys(Boc)-Asp(Q(t-Bu))—OH

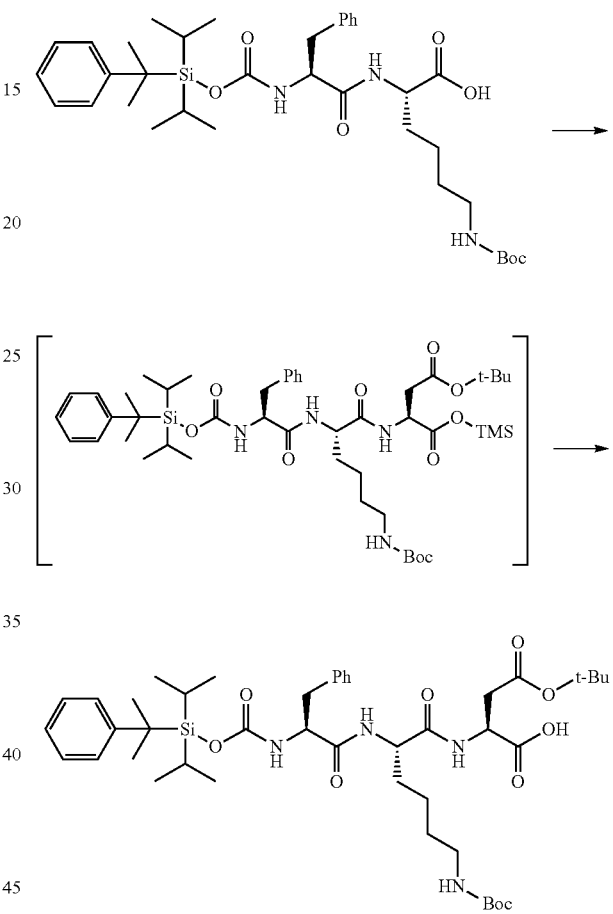

IPCSoc-Phe-Lys(Boc)-OH (0.32 g, 0.47 mmol) and N-methylmorpholine (0.06 g, 0.58 mmol) were mixed with tetrahydrofuran (4.0 g), and isobutyl chloroformate (0.08 g, 0.56 mmol) was added thereto at 0° C. and the mixture was stirred for 5 minutes. To the solution was added a solution separately prepared by mixing H-Asp(O(t-Bu))—OH (0.12 g, 0.62 mmol), N,O-bis(trimethylsilyl)acetamide (0.25 g, 1.2 mmol) and tetrahydrofuran (1.9 g) and stirring at 55° C. for 0.5 hour, and the mixture was further stirred while maintaining to 0° C. for 3 hours. The obtained reaction mixture was diluted with ethyl acetate, and successively washed with a saturated aqueous sodium hydrogen carbonate solution, a saturated aqueous ammonium chloride solution and a saturated aqueous sodium chloride solution. The obtained organic layer was concentrated to obtain IPCSoc-Phe-Lys(Boc)-Asp(O(t-Bu))—OH (0.38 g, Yield: 97%) as a white solid.

MASS (ESI+) m/z; (M+H)+841.48

Synthetic Example 7: Synthesis of IPCSoc-Phe-Lys(Boc)-Asp(O(t-Bu))-Phe-Phe-OH

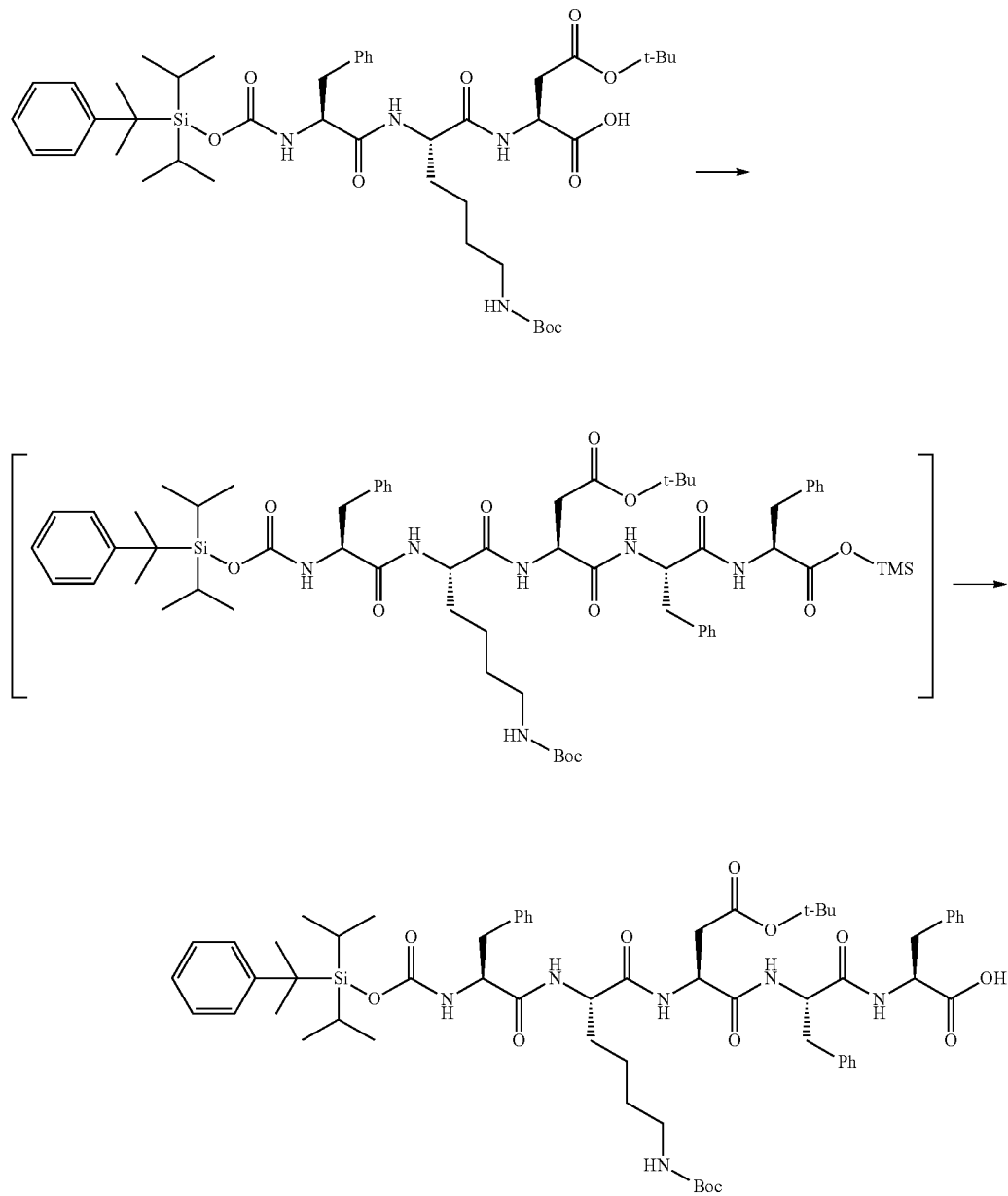

IPCSoc-Phe-Lys(Boc)-Asp(O(t-Bu))—OH (0.20 g, 0.24 mmol) and N-methyl-morpholine (0.03 g, 0.29 mmol) were mixed with tetrahydrofuran (2.0 g), isobutyl chloroformate (0.04 g, 0.27 mmol) was added thereto at 0° C. and the mixture was stirred for 5 minutes. With the solution was mixed a solution separately prepared by mixing H-Phe-Phe-OH (0.16 g, 0.51 mmol), N,O-bis(trimethylsilyl)acetamide (0.25 g, 1.2 mmol) and tetrahydrofuran (1.2 g), stirring at 55° C. for 20 minutes, and further adding N,O-bis(trimethylsilyl)acetamide (0.08 g, 0.41 mmol), and the mixture was further stirred while maintaining to 0° C. for 1 hour. The obtained reaction mixture was diluted with ethyl acetate, and successively washed with a saturated aqueous sodium hydrogen carbonate solution twice, a saturated aqueous ammonium chloride solution and a saturated aqueous sodium chloride solution. The obtained organic layer was concentrated to obtain IPCSoc-Phe-Lys(Boc)-Asp(O(t-Bu))-Phe-Phe-OH (0.29 g, Yield: 108%) as a white solid.

MASS (ESI+) m/z; (M+H)+1135.61

Synthetic Example 8: Synthesis of IPCSoc-Phe-Lys(BocVAsp(O(t-Bu))-Phe-Phe-Phe-OH

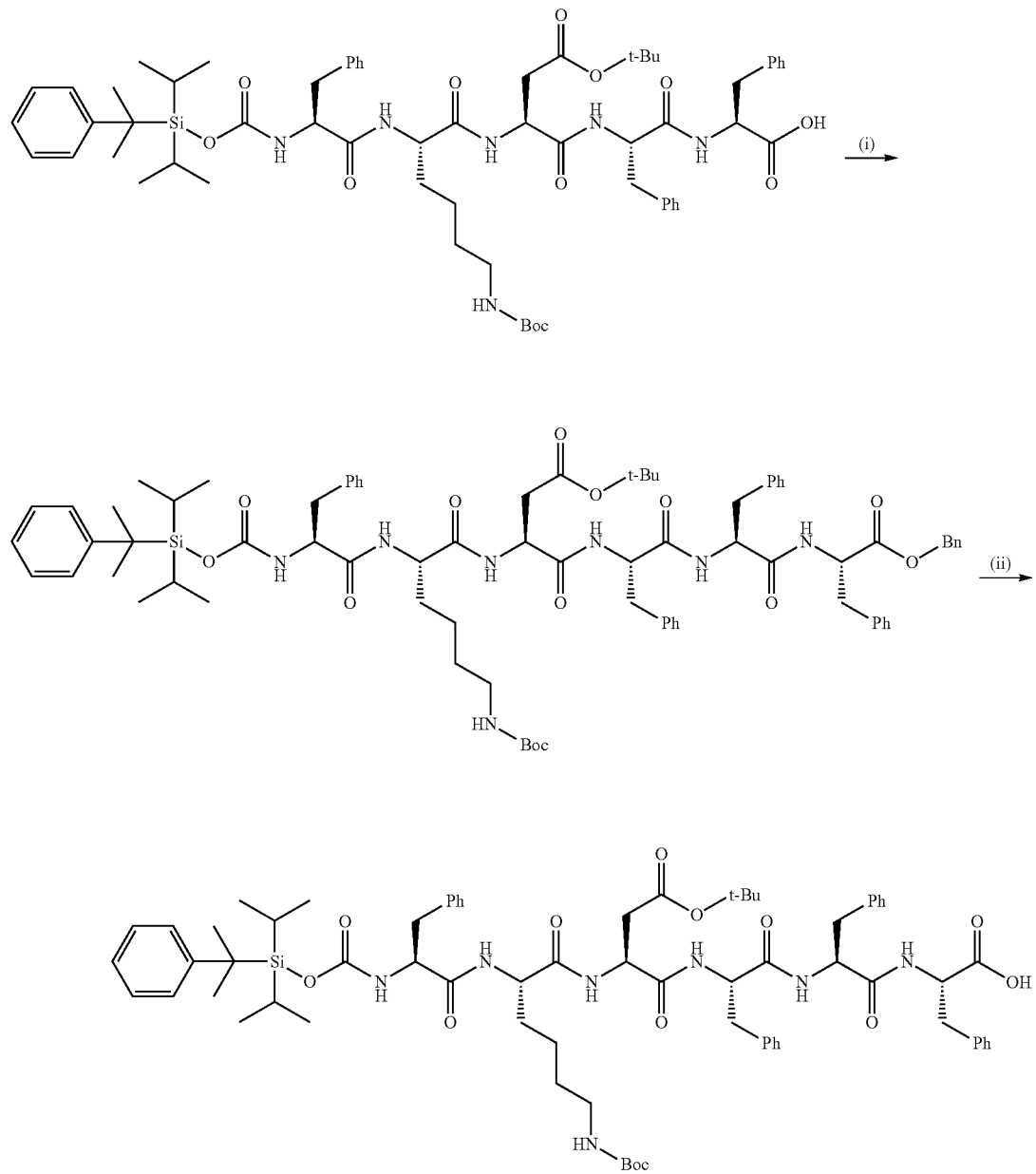

(i) IPCSoc-Phe-Lys(Boc)-Asp(O(t-Bu))-Phe-Phe-OH (0.25 g, 0.22 mmol) and H-Phe-OBn hydrochloride (0.08 g, 0.27 mmol) were mixed with methylene chloride (2.6 g), and after cooling to 0° C., N,N-diisopropylethylamine (0.07 g, 0.57 mmol) and (1-cyano-2-ethoxy-2-oxoethylideneaminooxy)dimethylamino-morpholino-carbenium hexafluorophosphate (0.12 g, 0.27 mmol) were added thereto and the mixture was stirred for 3 hours. The obtained reaction mixture was diluted with ethyl acetate, and then, successively washed with a saturated aqueous ammonium chloride solution, a saturated aqueous sodium hydrogen carbonate solution twice, a saturated aqueous ammonium chloride solution and a saturated aqueous sodium chloride solution. The obtained organic layer was concentrated and purified by silica gel column chromatography to obtain IPCSoc-Phe-Lys(Boc)-Asp(O(t-Bu))-Phe-Phe-Phe-OBn (0.22 g, Yield: 73%) as a white solid.

MASS (ESI+) m/z; (M+H)+1372.73

(ii) IPCSoc-Phe-Lys(Boc)-Asp(O(t-Bu))-Phe-Phe-Phe-OBn (0.05 g, 0.04 mmol) was mixed with ethyl acetate (1.0 g), and after adding 10 wt % Pd—C (0.01 g) thereto, the mixture was stirred under a hydrogen gas atmosphere at room temperature for 5 hours. After filtrating the reaction mixture, the obtained filtrate was concentrated to obtain IPCSoc-Phe-Lys(Boc)-Asp(O(t-Bu))-Phe-Phe-Phe-OH (0.05 g, Yield: 99%).

MASS (ESI+) m/z; (M+H)+1282.64

Synthetic Example 9: Synthesis of H-Phe-Lys(Boc)-Asp(Q(t-Bu))-Phe-Phe-Phe-OH

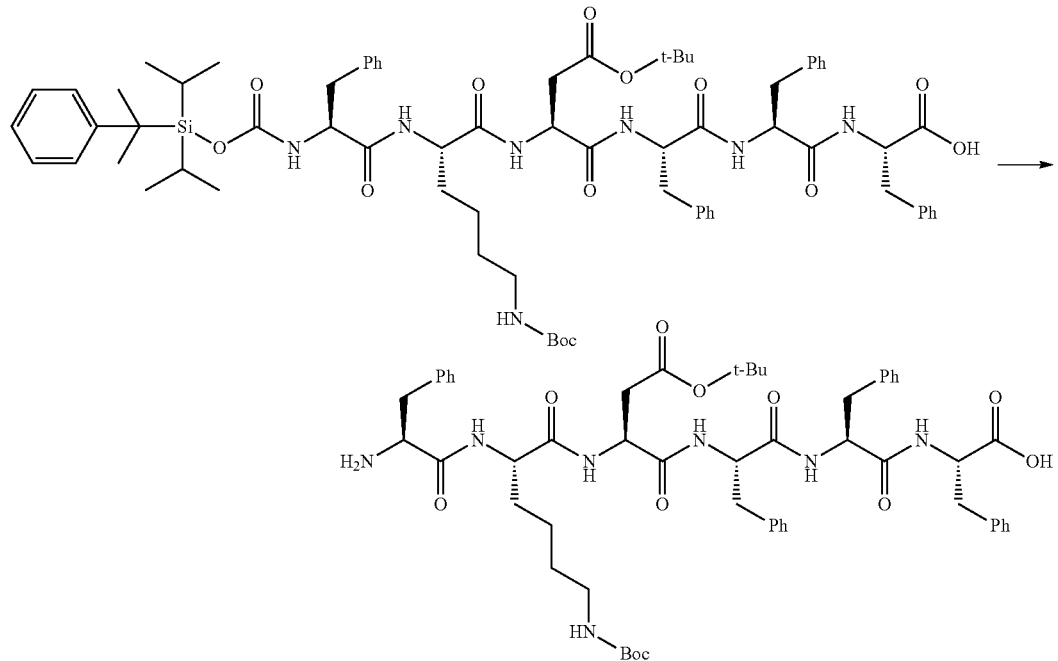

IPCSoc-Phe-Lys(Boc)-Asp(O(t-Bu))-Phe-Phe-Phe-OH (19.7 mg, 0.02 mmol) was mixed with methanol (1.0 g), and potassium fluoride (3.4 mg, 0.06 mmol) was added thereto at room temperature and the mixture was stirred for 4 hours. The obtained reaction mixture was washed with hexane (2.0 g) three times, and a 5 wt % aqueous ammonium chloride solution was added to the obtained methanol layer to precipitate the solid and it was filtered. The obtained solid was dried to obtain H-Phe-Lys(Boc)-Asp(O(t-Bu))-Phe-Phe-Phe-OH (12.6 mg, Yield: 74%) as a white solid.

MASS (ESI+) m/z; (M+H)+1006.52

Synthetic Example 10: Synthesis of H-Phe-Lys(Boc)-Asp(Q(t-Bu))-Phe-Phe-Phe-OBn

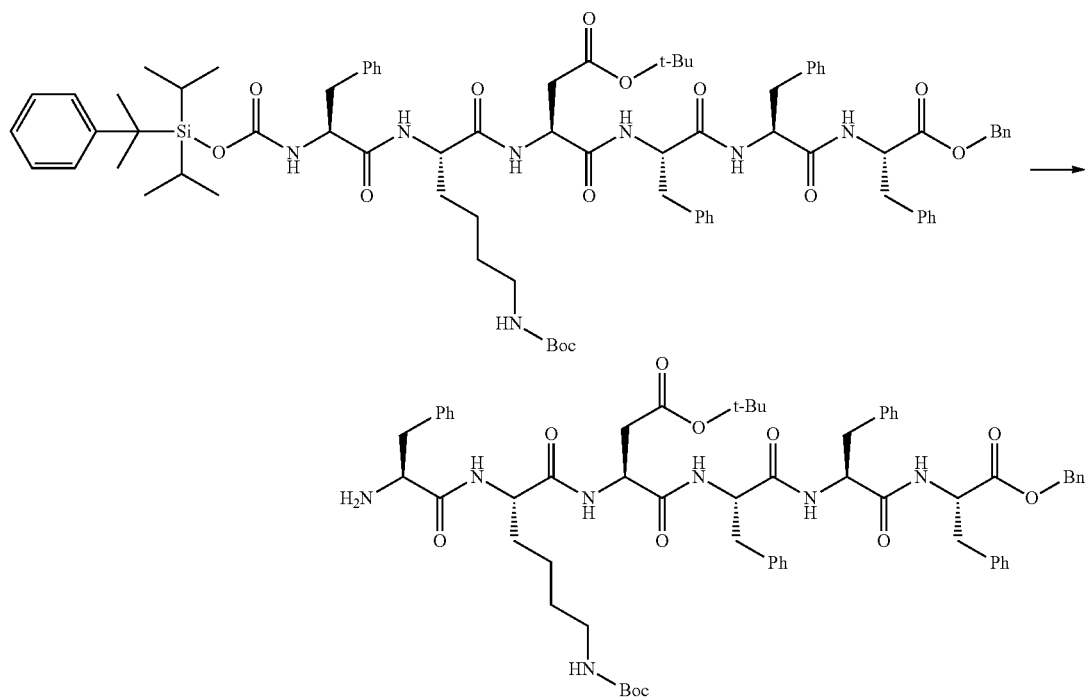

IPCSoc-Phe-Lys(Boc)-Asp(O(t-Bu))-Phe-Phe-Phe-OBn (0.15 g, 0.11 mmol) was mixed with methanol (3.0 g) and N-methylpyrrolidone (2.0 g), and potassium fluoride (0.02 g, 0.26 mmol) was added thereto at room temperature and the mixture was stirred for 3 hours. Water (2.0 g) was added to the obtained reaction mixture, and the mixture was washed with hexane (5.0 g) three times. Ethyl acetate and saturated brine were added to the obtained aqueous layer and the liquids were separated. The obtained organic layer was concentrated, and then, water (5.0 g) was added thereto to precipitate a solid and the solid was filtered. The obtained solid was dried to obtain H-Phe-Lys(Boc)-Asp(O(t-Bu))-Phe-Phe-Phe-OBn (0.12 g, Yield: 96%) as a white solid.

MASS (ESI+) m/z; (M+H)+1096.57

Reference Synthetic Example 10: Synthesis of CHBS-OTf

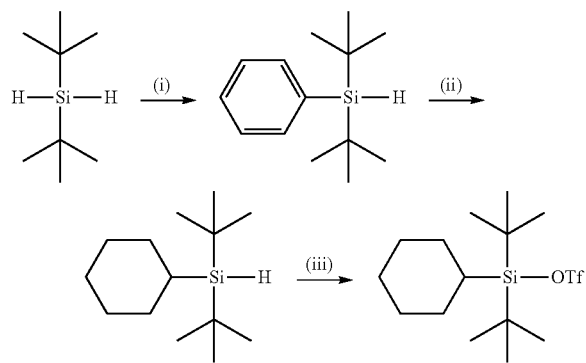

(i) Bromobenzene (5.7 g, 36 mmol) and tetrahydrofuran (8.0 g) were mixed, and after adding the mixture to 1.55M n-butyl lithium hexane solution (35 mL, 54 mmol) at 0° C., the mixture was stirred at 25° C. for 6 hours. To the obtained mixture was added a mixed solution of t-butyldihydrosilane (2.0 g, 13.9 mmol) and tetrahydrofuran (4.0 g), and the mixture was stirred at room temperature for 15 hours. The obtained reaction mixture was successively washed with 2M hydrochloric acid (14 g) and a 5 wt % aqueous sodium chloride solution (14 g). The obtained organic layer was concentrated, and hexane and silica gel were added thereto and the mixture was filtered. The obtained organic layer was concentrated to obtain a hexane solution (6.7 g) of PhBS—H.

(ii) The hexane solution (6.7 g) of PhBS—H and hexane (21 g) were mixed, and after adding Ru—Al (0.61 g) thereto, the mixture was stirred under a hydrogen gas atmosphere at 30° C. for 19 hours. The reaction mixture was filtered and the obtained filtrate was concentrated to obtain a hexane solution (5.9 g) of CHBS—H.

(iii) The hexane solution (0.4 g) of CHBS—H was mixed with methylene chloride (1.0 g), and after adding trifluoromethanesulfonic acid (0.14 g, 0.93 mmol) dropwise thereto under ice-cooling, the temperature of the mixture was raised to room temperature and the mixture was stirred for 0.5 hour. The formed CHBS-OTf was used in the next reaction as a hexane-methylene chloride solution without isolation.

Reference Synthetic Example 11: Synthesis of CHBSoc-Phe-OH

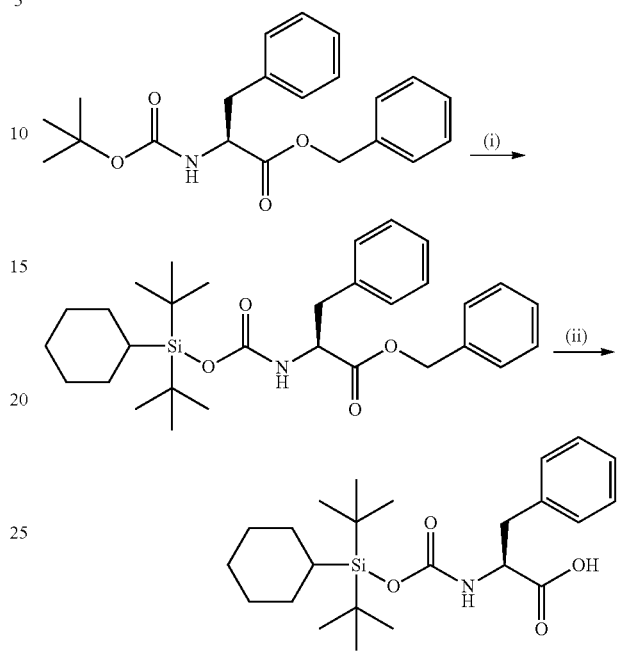

(i) Boc-Phe-OBn (0.20 g, 0.55 mmol) and lutidine (0.12 g, 1.1 mmol) were mixed with acetonitrile (2.0 g), and after adding the hexane-methylene chloride solution of CHBS-OTf at 0° C., the mixture was stirred at room temperature for 19 hours. After adding water (1.0 g) to the obtained reaction mixture, the precipitated solid was collected by filtration to obtain CHBSoc-Phe-OBn (0.21 g, Yield: 74%) as a white solid.

MASS (ESI+) m/z; (M+H)+524.30

(ii) CHBSoc-Phe-OBn (0.20 g, 0.38 mmol) was mixed with ethyl acetate (4.0), and after adding 10 wt % Pd—C (24.1 mg) thereto, the mixture was stirred under a hydrogen gas atmosphere at room temperature for 2 hours. The reaction mixture was filtered and the obtained filtrate was concentrated to obtain CHBSoc-Phe-OH (0.17 g, Yield: 100%).

MASS (ESI+) m/z; (M+H)+434.27

Synthetic Example 11: Synthesis of CHBSoc-Phe-Ala-OH

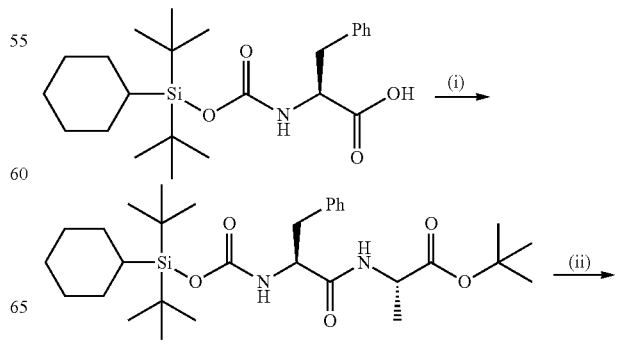

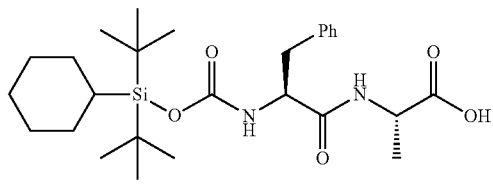

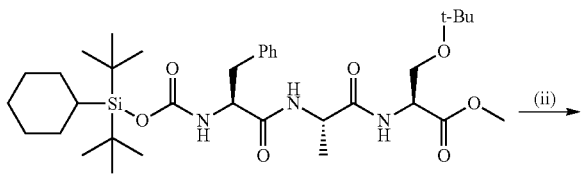

(i) CHBSoc-Phe-OH (0.50 g, 1.2 mmol) and H-Ala-O(t-Bu) hydrochloride (0.25 g, 1.4 mmol) were mixed with methylene chloride (5.2 g), and after cooling to 0° C., N,N-diisopropylethylamine (0.38 g, 2.9 mmol) and (1-cyano-2-ethoxy-2-oxoethylidene-aminooxy)dimethyl-amino-morpholino-carbenium hexafluorophosphate (0.60 g, 1.4 mmol) were added thereto and the mixture was stirred for 1 hour. The obtained reaction mixture was diluted with ethyl acetate, and then, successively washed with a saturated aqueous ammonium chloride solution, a saturated aqueous sodium hydrogen carbonate solution three times, a saturated aqueous ammonium chloride solution and a saturated aqueous sodium chloride solution. The obtained organic layer was concentrated to obtain CHBSoc-Phe-Ala-O(t-Bu) (0.68 g, Yield: 106%) as a pale yellowish solid.

MASS (ESI+) m/z; (M+H)+561.37

(ii) CHBSoc-Phe-Ala-O(t-Bu) (0.60 g, 1.1 mmol) was mixed with methylene chloride (12 g), and after cooling to 0° C., trifluoroacetic acid (4.9 g, 43.1 mmol) was added thereto, the temperature of the mixture was raised to room temperature and the mixture was stirred for 1 hour. The obtained reaction mixture was diluted with ethyl acetate, and then, successively washed with a saturated aqueous sodium hydrogen carbonate solution twice, a saturated aqueous ammonium chloride solution and a saturated aqueous sodium chloride solution. The obtained organic layer was concentrated to obtain CHBSoc-Phe-Ala-OH (0.52 g, Yield: 97%) as a white solid.

MASS (ESI+) m/z; (M+H)+505.31

Synthetic Example 12: Synthesis of CHBSoc-Phe-Ala-Ser(t-Bu)-OH

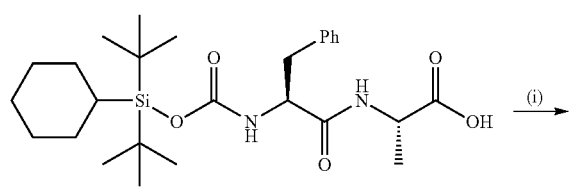

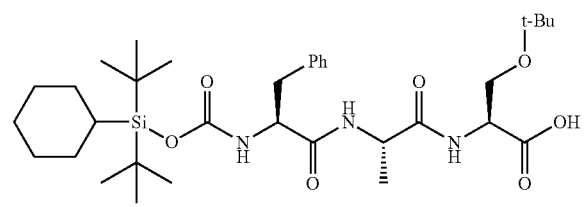

(i) CHBSoc-Phe-Ala-OH (0.52 g, 1.0 mmol) and H-Ser(t-Bu)-OMe hydrochloride (0.26 g, 1.2 mmol) were mixed with methylene chloride (5.0 g), and after cooling to 0° C., N,N-diisopropylethylamine (0.32 g, 2.5 mmol) and (1-cyano-2-ethoxy-2-oxoethylidene-aminooxy)dimethyl-amino-morpholino-carbenium hexafluorophosphate (0.51 g, 1.2 mmol) were added thereto and the mixture was stirred for 2 hours. The obtained reaction mixture was diluted with ethyl acetate, and then, successively washed with a saturated aqueous ammonium chloride solution, a saturated aqueous sodium hydrogen carbonate solution three times and a saturated aqueous sodium chloride solution. The obtained organic layer was concentrated to obtain CHBSoc-Phe-Ala-Ser(t-Bu)-OMe (0.73 g, Yield: 106%) as a pale yellowish solid.

MASS (ESI+) m/z; (M+H)+662.42

(ii) CHBSoc-Phe-Ala-Ser(t-Bu)-OMe (0.40 g, 0.60 mmol) was mixed with methanol (8.0 g), and after cooling to 0° C., a 5 wt % aqueous lithium hydroxide solution (1.2 g, 2.4 mmol) was added thereto, the temperature of the mixture was raised to room temperature and the mixture was stirred for 3 hours. The obtained reaction mixture was diluted with ethyl acetate, and then, successively washed with a saturated aqueous ammonium chloride solution and a saturated aqueous sodium chloride solution. The obtained organic layer was concentrated to obtain CHBSoc-Phe-Ala-Ser(t-Bu)-OH (0.36 g, Yield: 91%) as a brown solid.

MASS (ESI+) m/z; (M+H)+648.40

Synthetic Example 13: Synthesis of H-Phe-Ala-Ser(t-Bu)-Phe-OBn

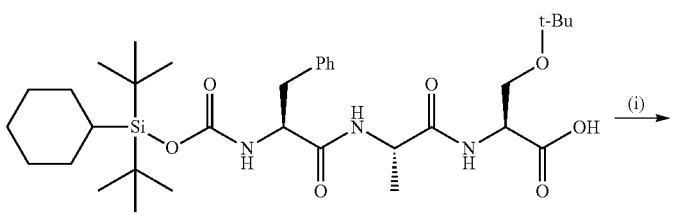

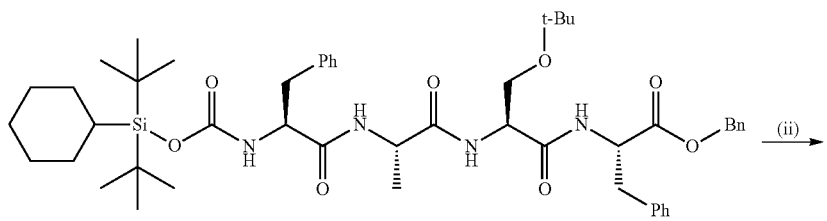

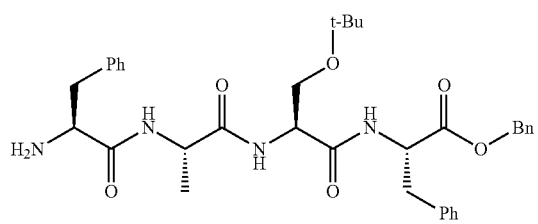

(i) CHBSoc-Phe-Ala-Ser(t-Bu)-OH (0.35 g, 0.54 mmol) and H-Phe-OBn hydrochloride (0.21 g, 0.72 mmol) were mixed with methylene chloride (4.0 g), and after cooling to 0° C., N,N-diisopropylethylamine (0.20 g, 1.5 mmol) and (1-cyano-2-ethoxy-2-oxoethylideneaminooxy)dimethylamino-morpholino-carbenium hexafluorophosphate (0.31 g, 0.72 mmol) were added thereto and the mixture was stirred for 2 hours. The obtained reaction mixture was diluted with ethyl acetate, and then, successively washed with a saturated aqueous ammonium chloride solution, a saturated aqueous sodium hydrogen carbonate solution twice and a saturated aqueous sodium chloride solution. The obtained organic layer was concentrated and purified by silica gel column chromatography to obtain CHBSoc-Phe-Ala-Ser(t-Bu)-Phe-OBn (0.35 g, Yield: 73%) as a white solid.

MASS (ESI+) m/z; (M+H)+885.51

(ii) CHBSoc-Phe-Ala-Ser(t-Bu)-Phe-OBn (0.10 g, 0.11 mmol) was mixed with methanol (2.0 g), and ammonium fluoride (0.05 g, 1.2 mmol) was added thereto under room temperature and the mixture was stirred for 4 hours. The obtained reaction mixture was washed with heptane (2.0 g) three times, and ethyl acetate and saturated brine were added to the obtained methanol layer and the liquids were separated. The obtained organic layer was concentrated to obtain H-Phe-Ala-Ser(t-Bu)-Phe-OBn (0.07 g, Yield: 98%) as a white solid.

MASS (ESI+) m/z; (M+H)+617.33

Synthetic Example 14: Synthesis of H-Phe-Ala-Ser(t-Bu)-Phe-OBn

CHBSoc-Phe-Ala-Ser(t-Bu)-Phe-OBn (0.15 g, 0.17 mmol) obtained in Step (i) of Synthetic Example 13 was mixed with tetrahydrofuran (3.1 g), and a 1M tetrabutylammonium fluoride-tetrahydrofuran solution (0.2 mL, 0.20 mmol) was added thereto under room temperature and the mixture was stirred for 2 hours. The obtained reaction mixture was diluted with ethyl acetate, and then, successively washed with a saturated aqueous ammonium chloride solution and a saturated aqueous sodium chloride solution. The obtained organic layer was concentrated, and after mixing with acetonitrile (3.0 mL), the mixture was washed with heptane (3.0 mL) twice. The obtained organic layer was concentrated to obtain H-Phe-Ala-Ser(t-Bu)-Phe-OBn (0.10 g, Yield: 95%) as a white solid.

MASS (ESI+) m/z; (M+H)+617.33

Reference Synthetic Example 12: Synthesis of H-Phe-Phe-OMe

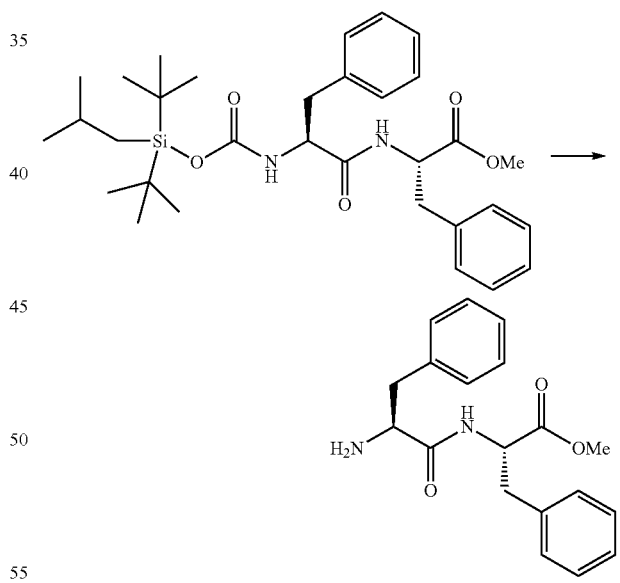

BIBSoc-Phe-Phe-OMe (0.10 g, 0.17 mmol) obtained in Step (i) of Synthetic Example 2 was mixed with methanol (2.0 g), potassium fluoride (0.02 g, 0.35 mmol) was added thereto under room temperature and the mixture was stirred for 5 hours. The obtained reaction mixture was washed with hexane (3.0 g) three times, and ethyl acetate and saturated brine were added to the obtained methanol layer and the liquids were separated. The obtained organic layer was concentrated to obtain H-Phe-Phe-OMe (0.07 g, Yield: 86%) as a white solid.

MASS (ESI+) m/z; (M+H)+327.16

Test Example 1: Comparison of Yields of Peptide Elongation Step and Deprotection Step of C-Terminal by N-Protected Amino Acid in which Silylcarbamate-Based Protective Group Having Specific Structure Introduced at N-Terminal

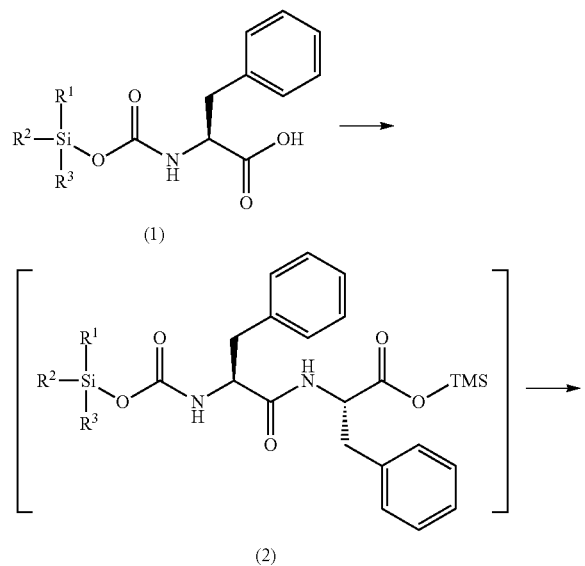

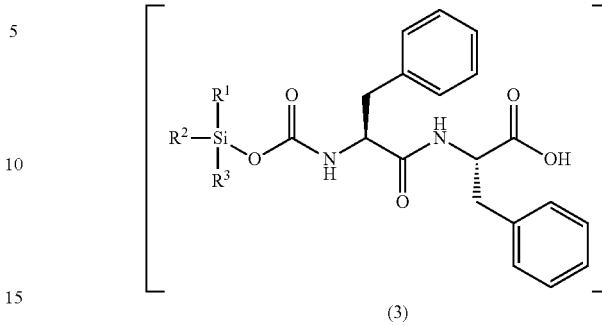

[Test Compound]

N-protected amino acids (hereinafter also referred to as starting material) in which a silylcarbamate-based protective group having a specific structure was introduced into the N-terminal described in the following Tables 1 and 2 were used. Incidentally, the starting materials can be obtained by the method described in Journal of Organic Chemistry, 1999, vol. 64, pp. 3792-3793, Journal of the American Chemical Society, 2005, vol. 127, pp. 13720-13725 and Reference Synthetic Examples 1, 5, 6 and 7, and a method equivalent thereto.

TABLE 1

| Starting material (1) | BBSoc-Phe-OH | IPCSoc-Phe-OH |
|---|---|---|
| Structural formula | *(structure)* | *(structure)* |
| MASS (ESI+) m/z; | (M + H) + 442.24 | (M + H) + 442.24 |

TABLE 2

| Starting material (1) | CHBSoc-Phe-OH | ODBSoc-Phe-OH |
|---|---|---|
| Structural formula | *(structure)* | *(structure)* |
| MASS (ESI+) m/z; | (M + H) + 434.27 | (M + H) + 604.46 |

[Test Method]

Each starting material (170 mg) and N-methylmorpholine (1.2 equivalent) were mixed with tetrahydrofuran (10-fold mass), and after cooling to 0° C., isobutyl chloroformate (1.1 equivalent) was added thereto and the mixture was stirred for 15 to 30 minutes. To the solution was added a solution separately prepared by mixing H-Phe-OH (1.2 equivalent), N,O-bis(tiimethylsilyl)acetamide (2.4 equivalent) and tetrahydrofuran (6-fold mass) and stirring at 50 to 55° C. for 0.5 to 1 hour, and the mixture was further stirred while maintaining to 0° C. for 1 to 3 hours. The obtained reaction mixture was diluted with t-butyl methyl ether (20-fold mass), and successively washed with a 10 wt % aqueous potassium carbonate solution (10-fold mass), a 20 wt % aqueous ammonium chloride solution (10-fold mass) and a saturated aqueous sodium chloride solution (10-fold mass). The obtained organic layer was concentrated and purified by silica gel column chromatography, and the yield of the objective material was calculated.

[Test Results]

Yields of the peptide elongation step and the deprotection step of the C-terminal using the respective starting materials were markedly improved as compared with the yield of Reference Synthetic Example 2.

TABLE 3

| Objective material (3) | BBSoc-Phe-Phe-OH | IPCSoc-Phe-Phe-OH |
|---|---|---|
| Yield | 94% | 93% |
| State | White solid | White solid |
| MASS (ESI+) m/z; | (M + H) + 589.31 | (M + H) + 589.3 |

TABLE 4

| Objective material (3) | CHBSoc-Phe-Phe-OH | ODBSoc-Phe-Phe-OH |
|---|---|---|
| Yield | 95% | 92% |
| State | White solid | Colorless oily product |
| MASS (ESI+) m/z; | (M + H) + 581.31 | (M + H) + 751.54 |

UTILIZABILITY IN INDUSTRY

According to the present invention, it can provide a method of producing a peptide with high efficiency.

The invention claimed is:

1. A method for producing a peptide, which comprises the following Steps (1) and (2):
    (1) a step of condensing a C-protected amino acid or a C-protected peptide to a C-terminal of an N-protected amino acid or an N-protected peptide represented by the formula (I):

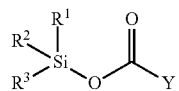

(I)

wherein,
Y represents an amino acid in which a C-terminal is unprotected or a peptide in which a C-terminal is unprotected,
$R^1$, $R^2$ and $R^3$ each independently represent an aliphatic hydrocarbon group which may have a substituent(s),
a total number of the carbon atoms in the $R^1R^2R^3Si$ group is 10 or more, and
the $R^1R^2R^3SiOC(O)$ group is bonded to the N-terminal in Y, and
    (2) a step of removing the protective group at the C-terminal of the peptide obtained in Step (1).

2. The producing method according to claim 1, which further comprises one or more repeating the following Steps (3) and (4):
    (3) a step of condensing the C-protected amino acid or the C-protected peptide to the C-terminal of the peptide obtained in Step (2) or (4), and
    (4) a step of removing the protective group at the C-terminal of the peptide obtained in Step (3).

3. The producing method according to claim 1, which comprises a step of purifying the obtained peptide by liquid separating.

4. The producing method according to claim 1, which comprises a step of purifying the obtained peptide by liquid separating with an acidic aqueous solution or a basic aqueous solution.

5. The producing method according to claim 1, wherein the protective group at the C-terminal of the C-protected amino acid or the C-protected peptide is a $C_{1-6}$ alkyl group, a $C_{7-10}$ aralkyl group or a tri-$C_{1-6}$ alkylsilyl group.

6. The producing method according to claim 1, wherein the protective group at the C-terminal of the C-protected amino acid or the C-protected peptide is a $C_{1-6}$ alkyl group or a tri-$C_{1-6}$ alkylsilyl group.

7. The producing method according to claim 1, wherein the protective group at the C-terminal of the C-protected amino acid or the C-protected peptide is a tri-$C_{1-6}$ alkylsilyl group.

8. The producing method according to claim 1, wherein the protective group at the C-terminal of the C-protected amino acid or the C-protected peptide is a tri-methylsilyl group.

9. The producing method according to claim 1, wherein the condensation in Step (1) is carried out by using a condensation agent selected from the group consisting of a carbodiimide-based condensation agent, a chloroformate-based condensation agent, an acid halide-based condensation agent, a phosphonium-based condensation agent and an uronium-based condensation agent.

10. The producing method according to claim 1, wherein the condensation in Step (1) is carried out using a condensation agent selected from the group consisting of isobutyl chloroformate, pivaloyl chloride and (1-cyano-2-ethoxy-2-oxoethylideneaminooxy)dimethylamino-morpholino-carbenium hexafluorophosphate.

11. The producing method according to claim 1, wherein a base is further used in Step (1).

12. The producing method according to claim 11, wherein the base is an aliphatic amine or an aromatic amine.

13. The producing method according to claim 11, wherein the base is N,N-diisopropylethylamine or N-methylmorpholine.

14. The producing method according to claim 1, wherein the deprotection conditions in Step (2) are conditions using a deprotecting agent other than the fluorine compound.

15. The producing method according to claim 1, wherein the deprotection conditions in Step (2) are conditions using water, a base or an acid, or using hydrogen and a metal catalyst.

16. The producing method according to claim 1, wherein the deprotection conditions in Step (2) are conditions using water, trifluoroacetic acid or lithium hydroxide, or using hydrogen and palladium carbon powder.

17. The producing method according to claim 7, wherein the deprotection conditions in Step (2) are conditions using water.

18. The producing method according to claim 1, which further comprises the following Step (5):
(5) a step of removing the protective group at the N-terminal of the peptide obtained in Step (2) or (4) with a deprotecting agent.

19. The producing method according to claim 18, wherein the deprotecting agent using in Step (5) is a fluorine compound.

20. The producing method according to claim 19, wherein the fluorine compound is potassium fluoride or ammonium fluoride.

21. The producing method according to claim 1, which further comprises the following Steps (6) and (7):
(6) a step of condensing a C-protected amino acid or C-protected peptide to the C-terminal of the peptide obtained in Step (2) or (4), and
(7) a step of removing the protective group at the N-terminal of the peptide obtained in Step (6) with a deprotecting agent.

22. The producing method according to claim 21, wherein the deprotecting agent using in Step (7) is a fluorine compound.

23. The producing method according to claim 22, wherein the fluorine compound is potassium fluoride or ammonium fluoride.

24. The producing method according to claim 21, wherein the protective group at the C-terminal of the C-protected amino acid or the C-protected peptide is a $C_{1-6}$ alkyl group or a benzyl group.

25. The producing method according to claim 1, wherein a total number of the carbon atoms in the $R^1R^2R^3Si$ group is 10 to 100.

26. The producing method according to claim 1, wherein a total number of the carbon atoms in the $R^1R^2R^3Si$ group is 10 to 40.

27. The producing method according to claim 1, wherein a total number of the carbon atoms in the $R^1R^2R^3Si$ group is 12 to 26.

28. The producing method according to claim 1, wherein two or three of $R^1$, $R^2$ and $R^3$ are each independently a secondary or tertiary aliphatic hydrocarbon group.

29. The producing method according to claim 28, wherein two of $R^1$, $R^2$ and $R^3$ are each independently a secondary aliphatic hydrocarbon group, and the remaining one is a tertiary aliphatic hydrocarbon group.

30. The producing method according to claim 29, wherein two of $R^1$, $R^2$ and $R^3$ are each independently a secondary $C_{3-6}$ alkyl group, and the remaining one is a tertiary $C_{4-6}$ alkyl group.

31. The producing method according to claim 1, wherein the $R^1R^2R^3Si$ group is a di-i-propyl-t-butylsilyl group.

32. The producing method according to claim 28, wherein two of $R^1$, $R^2$ and $R^3$ are each independently a secondary aliphatic hydrocarbon group, and the remaining one is a secondary aliphatic hydrocarbon group having a substituent, wherein the substituent of the secondary aliphatic hydrocarbon group exists on the carbon atom bonded to the silyl atom.

33. The producing method according to claim 32, wherein two of $R^1$, $R^2$ and $R^3$ are each independently a secondary $C_{3-6}$ alkyl group, and the remaining one is a secondary $C_{3-6}$ alkyl group substituted by a phenyl group, wherein the phenyl group which is a substituent of the secondary $C_{3-6}$ alkyl group exists on the carbon atom bonded to the silyl atom.

34. The producing method according to claim 33, wherein the $R^1R^2R^3Si$ group is a di-i-propylcumylsilyl group.

35. The producing method according to claim 28, wherein two of $R^1$, $R^2$ and $R^3$ are each independently a tertiary aliphatic hydrocarbon group.

36. The producing method according to claim 35, wherein two of $R^1$, $R^2$ and $R^3$ are each independently a tertiary $C_{4-6}$ alkyl group.

37. The producing method according to claim 36, wherein the $R^1R^2R^3Si$ group is a di-t-butylisobutylsilyl group.

38. The producing method according to claim 36, wherein the $R^1R^2R^3Si$ group is a benzyl-di-t-butylsilyl group, a di-t-butyloctadecylsilyl group or a di-t-butylcyclohexyl silyl group.

39. The producing method according to claim 1, wherein the amino acid or the peptide consists of an α-amino acid.

* * * * *